United States Patent
McInyre Caron

(10) Patent No.: US 10,363,229 B2
(45) Date of Patent: Jul. 30, 2019

(54) METHODS AND COMPOSITIONS FOR THE TREATMENT OF CANCER

(76) Inventor: Joan McInyre Caron, Thomaston, CT (US)

( * ) Notice: Subject to any disclaimer, the term of this patent is extended or adjusted under 35 U.S.C. 154(b) by 1975 days.

(21) Appl. No.: 13/382,263

(22) PCT Filed: Jun. 7, 2010

(86) PCT No.: PCT/US2010/037662
§ 371 (c)(1),
(2), (4) Date: Sep. 3, 2013

(87) PCT Pub. No.: WO2010/141956
PCT Pub. Date: Dec. 9, 2010

(65) Prior Publication Data
US 2016/0250158 A1    Sep. 1, 2016

Related U.S. Application Data

(60) Provisional application No. 61/331,168, filed on May 4, 2010, provisional application No. 61/184,500, filed on Jun. 5, 2009.

(51) Int. Cl.
| | |
|---|---|
| *A61K 9/70* | (2006.01) |
| *A61K 31/10* | (2006.01) |
| *A61K 45/06* | (2006.01) |
| *A61P 35/00* | (2006.01) |
| *A61P 35/04* | (2006.01) |

(52) U.S. Cl.
CPC ............ *A61K 31/10* (2013.01); *A61K 9/7023* (2013.01); *A61K 45/06* (2013.01); *A61P 35/00* (2018.01); *A61P 35/04* (2018.01)

(58) Field of Classification Search
CPC ...... A61K 31/10; A61K 45/06; A61K 9/7023; A61P 35/00; A61P 35/04
See application file for complete search history.

(56) References Cited

U.S. PATENT DOCUMENTS

| | | | |
|---|---|---|---|
| 8,188,047 B2 * | 5/2012 | Perez ................... | A61K 9/0014 514/21.9 |
| 2005/0118241 A1 | 6/2005 | Landschaft | |
| 2005/0118291 A1 | 6/2005 | Wang et al. | |
| 2005/0250757 A1 | 11/2005 | Hofmann | |
| 2006/0263434 A1 * | 11/2006 | Desai ................... | A61K 9/0019 424/489 |

FOREIGN PATENT DOCUMENTS

WO    2007005670 A2    1/2007

OTHER PUBLICATIONS

The Overnight Cure for Cancer, Psycho-Oncology D i s c o v e r H o w P r o l o n g e d C h r o n i c S t r e s s C a u s e s C a n c e r a n d H e a l W i t h i n . . . .*
Ebisuzaki K: "Aspirin and Methylsulfonylmethane (MSM): A Search for Common Mechanisms, With Implications for Cancer Prevention", Anticancer Research, vol. 23, No. 1A, Jan. 1, 2003, pp. 453-458, XP008068836.
McCabe D. et al: "Polar Solvents in the Chemoprevention of Dimethylbenzanthracene-Induced Rat Mammary Cancer", Archives of Surgery, American Medical Association, Chicago, IL, US, vol. 121, No. 12, Dec. 1, 1986, pp. 1455-1459, XP008059029.
Patrick J. O'Dwyer et al: "Use of polar solvents in chemoprevention of 1,2-dimethylhydrazine-induced colon cancer", vol. 62, No. 5, Sep. 1, 1988, pp. 944-948, XP55039718.
Wang M-Y et al: "Preventative Effect of Methylsulfonymethane (MSM) at the Initiation Stage of Mammary Carcinogenesis Induced by DMBA in Female SD Rats", Proceedings of the American Association for Cancer Research, AACR, US, vol. 44, Jul. 1, 2003, p. 684, XP008068886. Abstract No. 3445.

* cited by examiner

*Primary Examiner* — Snigdha Maewall
(74) *Attorney, Agent, or Firm* — McCarter & English, LLP; Jonathan M. Sparks; Joseph A. Ciardi

(57) ABSTRACT

The instant invention provides methods and compositions for the treatment and prevention of cell proliferative disorders.

26 Claims, 14 Drawing Sheets

First 10min After Adding 2% Methyl Sulfone. AVI.

Melanoma Cells with and without 2% methyl sulfone.
See attached movies for each frame.

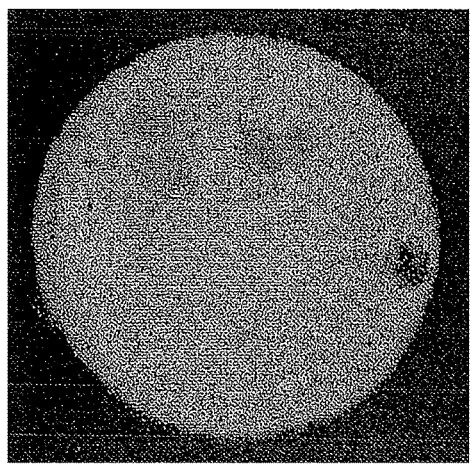
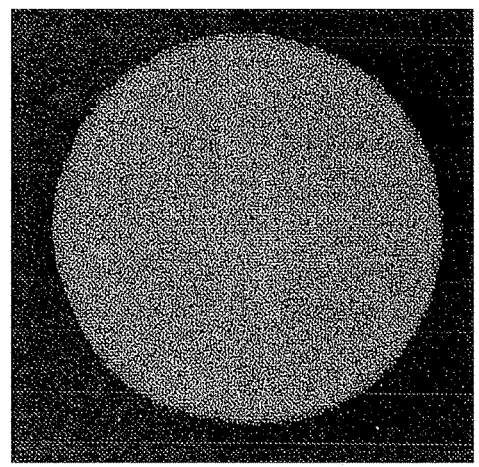
| Control | 2% Methyl Sulfone |
|---|---|
| 65 | 0 |
| 54 | 0 |
| 64 | 0 |
| 39 | 0 |
| 93 | 0 |
| 55 | 0 |
| 75 | 0 |
| 90 | 0 |
Number of colonies grown on soft agar. Cells were incubated for 14 days with and without 2% methyl sulfone before counting colonies. Results from eight control plates and eight 2% methyl sulfone plates are shown in the table.
FIG. 5

Migration of melanoma cells through a matrix membrane after being treated with 2% methyl sulfone for 48 hours. Dark spots are membrane pores; melanoma cells are lightly-colored and triangular. In the presence of 2% methyl sulfone, melanoma cells do not pass through the matrix membrane.

Wound healing in melanoma cells in the presence and absence of 2% methyl sulfone.

2% methyl sulfone induced senescence, as indicated by the blue stain, in melanoma cells. Virtually no control cells were senescent.

Arborization of melanoma cells that have been treated with 2% methyl sulfone for four weeks. Shown are four different fields of the arborized cells. The dark arbors indicate the presence of melanosomes.

Immunofluorescence microscopy of proteins involved in the ETM Transition. Shown are melanoma cells with and without 2% methyl sulfone after one week.

Immunofluorescence microscopy of actin filaments in melanoma cells with and without 2% methyl sulfone after 72 hours.

Immunofluorescence microscopy of microtubules in melanoma cells in the presence of 2% methyl sulfone over time.

Immunofluorescence microscopy of microtubules in melanoma cells with and without 2% methyl sulfone, in the presence of $10^{-7}$ M vinblastine (VNB). Cells were processed for immunofluorescence two hours after adding VNB.

METHODS AND COMPOSITIONS FOR THE TREATMENT OF CANCER

RELATED APPLICATIONS

This application is a continuation of PCT/US2010/037662 filed on Jun. 7, 2010, which claims the benefit of U.S. Provisional Application No. 61/184,500, filed Jun. 5, 2009, and U.S. Provisional Application No. 61/184,500, filed May 4, 2010. The entire contents of each of the aforementioned applications is hereby incorporated herein by reference.

BACKGROUND OF THE INVENTION

According to the world health organization (WHO), more than 11 millions people are diagnosed with cancer every year in the world and more than 7 millions people die from cancer every year. Conventional therapies for cancer involve the administration of anti-tumor drugs such as thymidylate synthase inhibitors (e.g., 5-fluorouracil), nucleoside analogs, non-steroidal and steroidal aromatase inhibitors, taxanes and topoisomerase-I inhibitors. The best outcome expected from present day chemotherapy is to kill malignant cells. A clinically significant problem with this approach is that the doses of current chemotherapeutic drugs required for this outcome are often toxic to non-cancerous cells. It would be beneficial to identify a chemotherapeutic drug that would render cancerous or malignant cells harmless to subjects while significantly decreasing the side effects associate with current chemotherapeutic drugs.

Accordingly, the need exists to identify or synthesize new chemotherapeutic agents that would effectively treat cell proliferative disorders while decreasing the side effects associated with current chemotherapeutic drugs.

SUMMARY OF THE INVENTION

The inventor of the instant application has discovered that methyl sulfone induces an irreversible non-malignant phenotype in aggressive, metastatic melanoma and breast cancer cells, which renders these cells harmless to subjects. Moreover, they inventors demonstrate that in the presence of methyl sulfone, the melanoma cells evolved into functional melanocytes. Accordingly, the instant application provides methods and compositions for the treatment of cell proliferative disorders, e.g., cancer.

Accordingly, in one aspect the instant invention provides methods for treating a cell proliferative disorder in a subject by administering to the subject a therapeutically effective amount of methyl sulfone, thereby treating the cell proliferative disorder. In one embodiment, the cell proliferative disorder is cancer. In a specific embodiment, the cancer is a solid tumor cancer, e.g., ovarian, brain, colon, lung, melanoma, bladder, breast or prostate cancer. In another embodiment, the cell proliferative disorder is a hematological cancer, e.g., leukemia or lymphoma.

In one embodiment, the subject had previously received chemotherapeutic or radiation therapy which was unsuccessful or less than completely successful.

In specific embodiments of the invention, methyl sulfone is administered systemically, locally, or targeted to the location of the cell proliferative disorder. In specific embodiments, the methyl sulfone is formulated in a micro or nanoparticle.

In another embodiment, the area comprising the solid tumor is sprayed with or bathed in methyl sulfone. In a related embodiment, all or a portion of the solid tumor is removed prior to treatment with methyl sulfone.

In one embodiment, the subject is a mammal, e.g., a human.

In another aspect, the instant invention provides methods of treating cancer in a subject in need thereof, comprising the step of: separately administering to the subject a composition comprising: methyl sulfone; and a chemotherapeutic agent. In one embodiment, the administration of methyl sulfone and the chemotherapeutic agent is simultaneous. In another embodiment, the administration of the composition methyl sulfone and the chemotherapeutic agent is sequential. In exemplary embodiments, the chemotherapeutic agent is doxil, topotecan, DNA-altering drugs, carboplatin, antimetabolites, gemcitabine, drugs that prevent cell division, vincristine, anti-angiogenic agents, or pazopanib.

In another aspect, the instant invention provides methods of treating a subject having a solid tumor surgically removed by spraying or bathing the area containing the tumor with methyl sulfone after removal of the tumor and prior to the completion of a surgical procedure.

In another aspect, the instant invention provides methods of treating ovarian cancer in a subject by contacting the ovaries with methyl sulfone, thereby treating ovarian cancer. In one embodiment, the ovaries are sprayed with methyl sulfone.

In another aspect, the instant invention provides methods of preventing the spread of cancer in subject having a solid tumor surgically removed by bathing or spraying the area containing the tumor with methyl sulfone after removal of the tumor and prior to the completion of the surgery, thereby preventing the spread of cancer in the subject.

In another aspect, the instant invention provides methods of inducing a cell to revert to a normal cellular phenotype from a cancer cell phenotype by contacting the cell with an effective amount of methyl sulfone, thereby inducing a phenotypic change from a cancer cell phenotype to a normal cell phenotype.

In another aspect, the instant invention provides pharmaceutical compositions comprising methyl sulfone and a pharmaceutically-acceptable diluent or carrier. In another embodiment, the composition comprises a gel, cream, solution, liposome or nanoparticle. In one embodiment, the composition comprises a delayed release dosage form. In another embodiment, the composition is formulated for aerosolization.

In another aspect, the instant invention provides a patch for the treatment of skin cancer comprising methyl sulfone. In one embodiment, the patch further comprises a pharmaceutically-acceptable diluent or carrier.

In another aspect, the instant invention provides kits for the treatment of a cell proliferative disorder comprising methyl sulfone and instructions for use. The kits may further comprise an applicator, e.g., a sponge, spray bottle, or aerosolizer.

DESCRIPTION OF THE DRAWINGS

FIG. 5 depicts a soft agar experiment demonstrating the growth of cell colonies in the absence of methyl sulfone and the absence of colonies in when treated with 2% methyl sulfone.

FIS. 9 depicts the arborization of melanoma cells that have been treated with 2% methyl sulfone for four weeks.

DETAILED DESCRIPTION OF THE INVENTION

Figure 1:
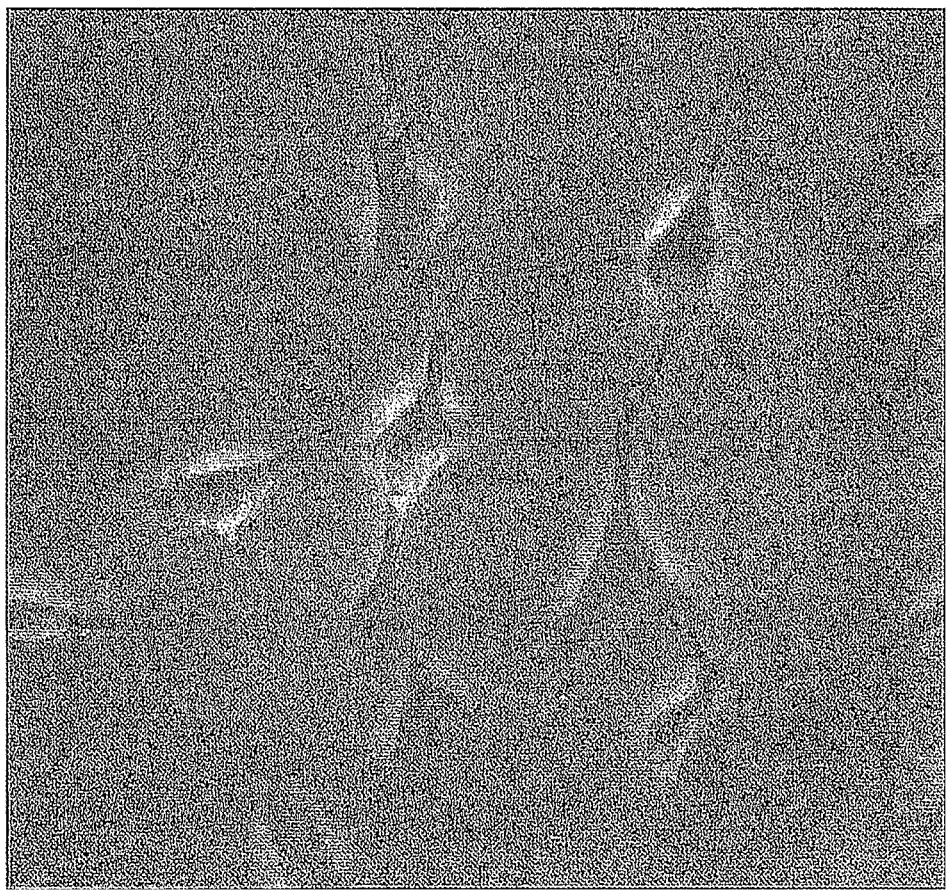
FIG. 1 is a single frame of a movie demonstrating the change in morphology of melanoma cells after the addition of 2% methyl sulfone. Cells became apoptotic at concentrations over 2% methyl sulfone.

The inventors have discovered that methyl sulfone is capable of arresting the progression of cancerous cells in a subject and can induce apoptosis at higher concentrations. Specifically, the inventors demonstrate that treatment of cancer cells with methyl sulfone induces several non-malignant phenotypes including contact inhibition, senescence and differentiation into arborized cells containing melanosomes. As described in the Examples, a comparison of induction of apoptosis in leukemic lymphocytes with lymphocytes isolated from a healthy volunteer showed that methyl sulfone induced apoptosis in more than 90% of the leukemic cells and induced apoptosis in less than 10% of T-cells from the healthy volunteer.

Methyl Sulfone

Methyl sulfone is also known in the literature as dimethyl sulfone, MSM and methyl sulfonyl methane. Methyl sulfone has the molecular formula $C_2H_6O_2S$ and the chemical structure:

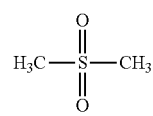

Methyl sulfone is non-toxic. Toxicity studies show that methyl sulfone is as toxic as water. Therefore, the side effects associated with current chemotherapeutic treatment are not a concern with methyl sulfone. Methyl sulfone has a molecular weight 94.13 and a CAS Registry Number of 67-71-0. The approximate water solubility of methyl sulfone is 150 g/L at 20° C. Methyl sulfone is stable and not hygroscopic.

Methyl sulfone has been shown to readily crosses plasma membranes to enter cells.

Cell Proliferative Disorders

The methods and compositions of the instant invention are useful in the treatment and prevention of cell proliferative disorders, e.g., cancer.

The term "cancer" includes malignancies characterized by deregulated or uncontrolled cell growth, for instance carcinomas, sarcomas, leukemias, and lymphomas. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

"Neoplasia" or "neoplastic transformation" is the pathologic process that results in the formation and growth of a neoplasm, tissue mass, or tumor. Such process includes uncontrolled cell growth, including either benign or malignant tumors. Neoplasms include abnormal masses of tissue, the growth of which exceeds and is uncoordinated with that of the normal tissues and persists in the same excessive manner after cessation of the stimuli that evoked the change. Neoplasms may show a partial or complete lack of structural organization and functional coordination with the normal tissue, and usually form a distinct mass of tissue. One cause of neoplasia is dysregulation of the cell cycle machinery.

Neoplasms tend to grow and function somewhat independently of the homeostatic mechanisms that control normal tissue growth and function. However, some neoplasms remain under the control of the homeostatic mechanisms that control normal tissue growth and function. For example, some neoplasms are estrogen sensitive and can be arrested by anti-estrogen therapy. Neoplasms can range in size from less than 1 cm to over 6 inches in diameter.

Neoplasms tend to morphologically and functionally resemble the tissue from which they originated. For example, neoplasms arising within the islet tissue of the pancreas resemble the islet tissue, contain secretory granules, and secrete insulin. Clinical features of a neoplasm may result from the function of the tissue from which it originated. For example, excessive amounts of insulin can be produced by islet cell neoplasms resulting in hypoglycemia which, in turn, results in headaches and dizziness. However, some neoplasms show little morphological or functional resemblance to the tissue from which they originated. Some neoplasms result in such non-specific systemic effects as cachexia, increased susceptibility to infection, and fever.

By assessing the histology and other features of a neoplasm, it can be determined whether the neoplasm is benign or malignant. Invasion and metastasis (the spread of the neoplasm to distant sites) are definitive attributes of malignancy. Despite the fact that benign neoplasms may attain enormous size, they remain discrete and distinct from the adjacent non-neoplastic tissue. Benign tumors are generally well circumscribed and round, have a capsule, and have a grey or white color, and a uniform texture. In contrast, malignant tumors generally have fingerlike projections, irregular margins, are not circumscribed, and have a variable color and texture. Benign tumors grow by pushing on adjacent tissue as they grow. As the benign tumor enlarges it compresses adjacent tissue, sometimes causing atrophy. The junction between a benign tumor and surrounding tissue may be converted to a fibrous connective tissue capsule allowing for easy surgical removal of the benign tumor.

Conversely, malignant tumors are locally invasive and grow into the adjacent tissues usually giving rise to irregular margins that are not encapsulated making it necessary to remove a wide margin of normal tissue for the surgical removal of malignant tumors. Benign neoplasms tend to grow more slowly and tend to be less autonomous than malignant tumors. Benign neoplasms tend to closely histologically resemble the tissue from which they originated. More highly differentiated cancers, i.e., cancers that resemble the tissue from which they originated, tend to have a better prognosis than poorly differentiated cancers, while malignant tumors are more likely than benign tumors to have an aberrant function, e.g., the secretion of abnormal or excessive quantities of hormones.

The histological features of cancer are summarized by the term "anaplasia." Malignant neoplasms often contain numerous mitotic cells. These cells are typically abnormal. Such mitotic aberrations account for some of the karyotypic abnormalities found in most cancers. Bizarre multinucleated cells are also seen in some cancers, especially those that are highly anaplastic.

The term "anaplasia" includes histological features of cancer. These features include derangement of the normal tissue architecture, the crowding of cells, lack of cellular orientation termed dyspolarity, and cellular heterogeneity in size and shape termed "pleomorphism." The cytologic features of anaplasia include an increased nuclear-cytoplasmic ratio (nuclear-cytoplasmic ratio can be over 50% for malignant cells), nuclear pleomorphism, clumping of the nuclear chromatin along the nuclear membrane, increased staining of the nuclear chromatin, simplified endoplasmic reticulum, increased free ribosomes, pleomorphism of mitochondria, decreased size and number of organelles, enlarged and increased numbers of nucleoli, and sometimes the presence of intermediate filaments.

The term "dysplasia" includes pre-malignant states in which a tissue demonstrates histologic and cytologic features intermediate between normal and anaplastic. Dysplasia is often reversible.

The term "carcinoma" includes malignancies of epithelial or endocrine tissues, including respiratory system carcinomas, gastrointestinal system carcinomas, genitourinary system carcinomas, testicular carcinomas, breast carcinomas, prostate carcinomas, endocrine system carcinomas, melanomas, choriocarcinoma, and carcinomas of the cervix, lung, head and neck, colon, and ovary. The term "carcinoma" also includes carcinosarcomas, which include malignant tumors composed of carcinomatous and sarcomatous tissues. The term "adenocarcinoma" includes carcinomas derived from glandular tissue or a tumor in which the tumor cells form recognizable glandular structures.

The term "sarcoma" includes malignant tumors of mesodermal connective tissue, e.g., tumors of bone, fat, and cartilage.

The terms "leukemia" and "lymphoma" include malignancies of the hematopoietic cells of the bone marrow. Leukemias tend to proliferate as single cells, whereas lymphomas tend to proliferate as solid tumor masses. Examples of leukemias include acute myeloid leukemia (AML), acute promyelocytic leukemia, chronic myelogenous leukemia, mixed-lineage leukemia, acute monoblastic leukemia, acute lymphoblastic leukemia, acute non-lymphoblastic leukemia, blastic mantle cell leukemia, myelodyplastic syndrome, T cell leukemia, B cell leukemia, and chronic lymphocytic leukemia. Examples of lymphomas include Hodgkin's disease, non-Hodgkin's lymphoma, B cell lymphoma, epitheliotropic lymphoma, composite lymphoma, anaplastic large cell lymphoma, gastric and non-gastric mucosa-associated lymphoid tissue lymphoma, lymphoproliferative disease, T cell lymphoma, Burkitt's lymphoma, mantle cell lymphoma, diffuse large cell lymphoma, lymphoplasmacytoid lymphoma, and multiple myeloma.

For example, the therapeutic methods of the present invention can be applied to cancerous cells of mesenchymal origin, such as those producing sarcomas (e.g., fibrosarcoma, myxosarcoma, liosarcoma, chondrosarcoma, osteogenic sarcoma or chordosarcoma, angiosarcoma, endotheliosardcoma, lympangiosarcoma, synoviosarcoma or mesothelisosarcoma); leukemias and lymphomas such as granulocytic leukemia, monocytic leukemia, lymphocytic leukemia, malignant lymphoma, plasmocytoma, reticulum cell sarcoma, or Hodgkin's disease; sarcomas such as leiomysarcoma or rhabdomysarcoma, tumors of epithelial origin such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, chorioaencinoma, semonoma, or embryonal carcinoma; and tumors of the nervous system including gioma, menigoma, medulloblastoma, schwannoma or epidymoma. Additional cell types amenable to treatment according to the methods described herein include those giving rise to mammary carcinomas, gastrointestinal carcinoma, such as colonic carcinomas, bladder carcinoma, prostate carcinoma, and squamous cell carcinoma of the neck and head region. Examples of cancers amenable to treatment according to the methods described herein include vaginal, cervical, and breast cancers.

The language "inhibiting undesirable cell growth" is intended to include the inhibition of undesirable or inappropriate cell growth. The inhibition is intended to include inhibition of proliferation including rapid proliferation. For example, the cell growth can result in benign masses or the inhibition of cell growth resulting in malignant tumors. Examples of benign conditions which result from inappropriate cell growth or angiogenesis are diabetic retinopathy, retrolental fibrioplasia, neovascular glaucoma, psoriasis, angiofibromas, rheumatoid arthritis, hemangiomas, Karposi's sarcoma, and other conditions or dysfunctions characterized by dysregulated endothelial cell division.

The language "inhibiting tumor growth" or "inhibiting neoplasia" includes the prevention of the growth of a tumor in a subject or a reduction in the growth of a pre-existing tumor in a subject. The inhibition also can be the inhibition of the metastasis of a tumor from one site to another. In particular, the language "tumor" is intended to encompass both in vitro and in vivo tumors that form in any organ or body part of the subject. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, esophagus, pancreas, rectum, parathyroid, thyroid, adrenal, neural tissue, head and neck, colon, stomach, bronchi, kidneys. Specifically, the tumors whose growth rate is inhibited by the present invention include basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas (i.e. maglinant lymphomas, mantle cell lymphoma), malignant melanomas, multiple myeloma, epidermoid carcinomas, and other carcinomas and sarcomas.

Pharmaceutical Compositions and Delivery Systems

The active composition of the invention methyl sulfone, can be incorporated into pharmaceutical compositions suitable for administration to a subject, e.g., a human. Such compositions typically comprise the methyl sulfone and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions. A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating methyl sulfone in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, methyl sulfone is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Methyl sulfone can also be formulated into nanoparticles for delivery to a subject. Nanoparticles have the ability to deliver high concentrations of a chemotherapeutic agent directly to cancer cells thereby avoiding delivery to healthy cells. Specifically, methyl sulfone nanoparticles can be used to deliver methyl sulfone directly to a specific tissue or organ to treat a cell proliferative disorder such as cancer.

Two specific exemplary targeting systems for nanoparticles are disclosed herein. First, one system will use antibodies against specific cell surface proteins expressed in adult cancer stem cells. For example CD44 in breast cancer stem cells will be targeted with nanoparticles having CD44 specific antibodies. The second targeting system will use tissue-specific antibodies against non-stem cell cancer cells. These cancer cells make up the vast majority of malignant cells. Alternatively, solid tumors can be targeted with nanoparticles loaded with methyl sulfone through the tumor's leaky vascular system.

Exemplary types of nanoparticles contemplated for use with the invention include liposomes and nanospheres.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The present invention encompasses pharmaceutically acceptable topical formulations of methyl sulfone. These topical formulations are useful for the treatment of, for example, melanoma. The term "pharmaceutically acceptable topical formulation", as used herein, means any formulation which is pharmaceutically acceptable for intradermal administration of a compound of the invention by application of the formulation to the epidermis.

In certain embodiments, the pharmaceutically acceptable topical formulations of the invention comprise at least methyl sulfone and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting methyl sulfone through the stratum corneum and into the epidermis or dermis. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

The pharmaceutical compositions can be included in a kit, container, pack, or dispenser together with instructions for administration.

As defined herein, a therapeutically effective amount of methyl sulfone is an amount which reduces, or eliminates the number of cancerous cells or the reduces the size of a tumor in a subject. As is understood by those of skill in the art, dosages differ depending on the route of administration. In exemplary embodiments, 0.2-0.6 mg methyl sulfone/ml solvent is used for spraying, topical, transdermal, or oral administration. In other exemplary embodiments, such as IV infusion or intrathecal infusion higher concentration of methyl sulfone could be used e.g., 1.0-5.0 mg/ml.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of methyl sulfone can include a single treatment or, preferably, can include a series of treatments. In a preferred example, a subject is treated with a solution of methyl sulfone in the range of 0.2 and 0.6 mg methyl sulfone/ml solvent, one time per week for between about 1 to 40 weeks, preferably between 5 to 20 weeks, more preferably between about 10 to 15 weeks. It will also be appreciated that the effective dosage of methyl sulfone used for treatment may increase or decrease over the course of a particular treatment. Changes in dosage may result and become apparent from the results of diagnostic assays that are known in the art for diagnosing or monitoring the progression on various types of cancer.

It is understood that appropriate doses of small molecule agents such as methyl sulfone depends upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the molecule to have.

Moreover, one of skill in the art will realize that specific types of cancer can be effectively targeted using specific modes of administration. Exemplary modes of administration for specific types of cancer are set forth in the table below:

| Delivery Systems | Types of Cancer |
| --- | --- |
| Intrathecal Pump | Brain, Spinal Cord |
| Direct Spray | Ovarian, Fallopian Tube |
| Aerosolize to inhale | Lung |
| Intra-bladder Instillation | Bladder |
| Transdermal patches | Melanoma |
| Oral-Delayed release | Colon |
| IV injection of Nanoparticles | Hematological Cancers such as Leukemia, Lymphoma, Multiple Myeloma; bone cancer; metastasis of any cancer |
| Urethral catherization or direct spray | Prostate |
| IV injection into primary blood supply | Breast |

Methods of Treatment

In yet another aspect, the present invention provides methods of treatment of various cell proliferative disorders, including, for example, breast, ovarian, lung, skin and hematological cancers, e.g., leukemia. In certain embodiments, according to the methods of treatment of the present invention, the growth and of tumor cells is inhibited by contacting the cells with an methyl sulfone as described herein.

The methods of the instant invention are effective for the treatment of cancer while significantly decreasing (or eliminating) many of the adverse effects associated with current chemotherapeutic treatment. As indicated above, methyl sulfone is non-toxic and therefore does not cause the side effects associated with most chemotherapeutic treatments. This allows for increased dosages to be administered to a subject in need of treatment.

As used herein, "subject" includes organisms which are capable of suffering from a cell proliferative disorder, e.g., cancer, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a cell proliferative disorder is meant to include subjects at risk of developing a cell proliferative disorder. In one embodiment, the subject is at greater risk than the average member of a population.

The language "a prophylactically effective amount" refers to an amount of a methyl sulfone or a pharmaceutical preparation thereof, which is effective, upon single or multiple dose administration to the subject, in preventing or treating a cell proliferative disorder.

The language "therapeutically effective amount" of methyl sulfone refers to an amount of methyl sulfone or a pharmaceutical preparation thereof which, upon single or multiple dose administration to the subject to provide a therapeutic benefit to the subject. In one embodiment, the therapeutic benefit is reducing or eliminating cancerous cells or tumors, or prolonging the survivability of a subject with a cell proliferative disorder.

Accordingly, in another aspect of the invention, methods for the treatment of cancer are provided comprising administering a therapeutically effective amount of methyl sulfone, to a subject in need thereof. In certain embodiments, a method for the treatment of cancer is provided comprising administering a therapeutically effective amount of methyl sulfone, or a pharmaceutical composition comprising an inventive compound to a subject in need thereof, in such amounts and for such time as is necessary to achieve the desired result.

In certain embodiments, the method involves the administration of a therapeutically effective amount of methyl sulfone or a pharmaceutically acceptable derivative thereof to a subject (including, but not limited to a human or animal) in need of it. In certain embodiments, methyl sulfone is useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

In certain embodiments, the present invention provides a methods for treating cell proliferative disorders in a subject comprising administering to a subject in need thereof a therapeutically effective amount of methyl sulfone, optionally with a pharmaceutically acceptable carrier, adjuvant or vehicle. Methyl sulfone can be administered in any manner known in the art such as those disclosed herein. A trained clinician will be able to choose the best route of administration based on the type and location of the cell proliferative disorder.

In another embodiment, the invention provides a prophylactic method of preventing a cell proliferative disorder, or preventing the recurrence of a cell proliferative disorder.

In one embodiment, a subject at risk for developing a cell proliferative disorder, or at risk of having a recurrence of a cell proliferative disorder is prophylactically administered methyl sulfone or a pharmaceutical composition comprising methyl sulfone so as to prevent the occurrence or reoccurrence of the cell proliferative disorder.

The instant invention also provides combination treatments. Treatment with methyl sulfone or a pharmaceutical composition thereof, can be combined with chemotherapeutic, radiation or surgical treatment.

In one embodiment, subject is administered one or more anti-cancer agents in combination with methyl sulfone to treat a cell proliferative disorder. the anticancer agent can be a chemotherapeutic agent or a biological agent, e.g., an anti-cancer antibody.

In another embodiment, is administered methyl sulfone in combination with surgical intervention to treat cancer. In a related embodiment, subjects having surgery to remove one or more tumors are treated with a solution of methyl sulfone to ensure that the successful treatment. In an exemplary embodiment, when a subject has surgery to remove one or more tumor from the abdomen, the abdominal cavity can be washed with a solution of methyl sulfone.

EXAMPLES

It should be appreciated that the invention should not be construed to be limited to the examples that are now described; rather, the invention should be construed to include any and all applications provided herein and all equivalent variations within the skill of the ordinary artisan.

Example 1: Effect of Methyl Sulfone on Cancer Cells

The following experiment demonstrates that methyl sulfone is capable of inducing apoptosis or senescence in cancer cells.

The following methods were used in Example 1:
Cell Culture

Cloudman S-91 mouse melanoma cells (sub-clone M-3, CCL 53.1; American Type Culture Collection, Rockville, Md.) were grown in RMPI medium supplemented with 10% fetal bovine serum (Invitrogen, Inc) and 5% penicillin-streptomycin (Invitrogen, Inc). Mouse breast cancer cells (66Cl-1; American Type Culture Collection, Rockville, Md.) that are estrogen-receptor negative were grown in DMEM medium supplemented with 10% fetal bovine serum (Invitrogen, Inc) and 5% penicillin/streptomycin (Invitrogen, Inc). Human T-cell leukemic lymphocytes (CEM; American Type Culture Collection, Rockville, Md.) were grown in MEM medium supplemented with 7% fetal calf serum. Cultures were passaged twice a week.

Normal T-cell lymphocytes were obtained from a blood sample of a healthy volunteer. Blood samples were obtained with IRB approval and with the volunteer signing an Informed Consent Form. White blood cells were separated from red blood cells using a Ficoll gradient. Flow cytometry with antibodies against CD3 and CD4 was used to identify T-cell lymphocytes (Flow Cytometry Facility, University of Connecticut Health Center, Farmington, Conn.).

Annexin Apoptosis Assay

Early and late apoptosis was assessed with the Annexin V-FITC Apoptosis Detection Kit from PharMingen (Becton-Dickinson, San Diego, Calif.). Images were obtained at the Center for Cell Analysis and Modeling, University of Connecticut Health Center, Farmington, Conn., with an Axioplan CCD Microscope equipped with a 40×1.3 NA FL objective lens and Photometrics PXL-EEV37 high speed digital cooled CCD camera via Metamorph image acquisition and analysis software (Universal Imaging Corp., Downington, Pa.).

Live Cell Microscopy

Cells were plated on 35 mm tissue culture dishes at concentration of $10^5$ cells/plate, unless stated otherwise, and incubated at 37° C., 5% $CO_2$. After 24 hours, methyl sulfone (0-10% in medium) was added to appropriate plates and immediately videotaped with a Nikon TE300 inverted microscope equipped with a 10×0.25 NA Plan Achromat objective lens. Control cells (no drug) were videotaped as described above. Time series (10 min) of phase contrast images were acquired at a video rate of 1 frame/5 s with a Watec-902B CCD video camera (Watec Corp., Japan) via the stream acquisition option of Metamorph image acquisition and analysis software (Universal Imaging Corp., Downington, Pa.). During recordings, cells were kept at 37° C. with 10 mM Hepes, pH 7.4. Time series of cells +/−2% methyl sulfone were obtained every 24-48 hours for up to 6 weeks.

Cell Proliferation

Cells were plated onto sterile 12 mm coverslips in 35 mm tissue culture plates and incubated at 37° C., 5% $CO_2$. After 24 hours, 2% methyl sulfone in medium or medium alone was added the plates and incubated at 37° C., 5% $CO_2$ for 48 and 72 hrs. BrdU (Molecular Probes, Eugene, Oreg., USA; diluted ⅓ in RPMI medium) was added to each plate for 60 minutes at 37° C., 5% $CO_2$. Coverslips were transferred to porcelain holders, washed with PBS, fixed in methanol/acetone (1:1), washed with PBS, and incubated in 5% BSA/PBS for 30 minutes at room temperature. To denature DNA, coverslips were placed in 0.1N HCL/1% Triton X-100 for 10 minutes at room temperature. After washing in PBS, cells were incubated with Alexa Fluor 488 anti-BrdU antibody (Molecular Probes, Eugene, Oreg.; diluted ¹⁄₂₀ in 5% BSA/PBS) for 60 minutes at room temperature. Cells were washed in PBS and incubated with Hoechst (diluted ¹⁄₁₀₀₀ in PBS) in the dark at room temperature. After washing in PBS, cells were dipped in $dH_2O$ and drained onto Kim Wipes. SlowFade mounting medium (Molecular Probes, Eugene, Oreg.) was added to a glass slide and coverslips were placed face down onto slides and sealed with clear nail polish. Cells were viewed at the Center for Cell Analysis and Modeling, University of Connecticut Health Center, Farmington, Conn., with an Axioplan CCD Microscope equipped with a 40×1.3 NA FL objective lens, equipped with a Photometrics PXL-EEV37 high speed digital cooled CCD camera. Molecular Devices Metamorph was used for image acquisition.

Immunofluorescence of Actin Filaments

Cells were plated onto 10-well slides ( ) that were pre-treated with sulfuric acid. After 24 hours, medium was removed and 2% methyl sulfone in medium was added to half the slides; control cells received medium alone. At 72 and 144 hours, cells were washed in 37° C. PBS, pH 7.4, and fixed in 3.7% formaldehyde in PBS for 10 minutes. PBS was used to wash cells three times followed by a wash in 0.1% Triton X-100/PBS for 5 minutes. Cells were again washed three times in PBS, then in 1% BSA/PBS for 20 minutes. Cells were incubated with Rhodamine-labeled Phalloidin (Molecular Probes, Eugene, Oreg.; diluted ¹⁄₄₀ in 1% BSA/PBS) for 20 minutes. After washing three times in PBS, SlowFade was added to each well. Glass coverslips were placed over each slide and sealed with nail polish. Images were visualized using 568-nm excitation on a Perkin Elmer Ultraview RS5 spinning-disk confocal scanning system mounted on a Nikon TE2000 inverted microscope with a 100×1.4 NA Plan Apo oil immersion objective. (William A. Mohler, Ph.D., Director, Spinning Disk Microscope Facility, University of Connecticut Health Center).

Immunofluorescence of E-Cadherin, β-Catenin and N-Cadherin

Cells were plated onto 12 mm coverslips. When cells grew to 60 to 70% confluence, 2% methyl sulfone was added to half the coverslips and normal medium to other half. After 24 hours, coverslips were dipped in 37° C. PBS for 30 seconds and fixed in 37° C. 4% paraformaldehyde for 10 minutes. Cells were washed in PBS for 5 minutes and incubated in 1% Triton X-100/PBS for 5 minutes. To block nonspecific sites, chicken serum was diluted ¹⁄₂₀ in PBS and added to cells for 30 minutes. Cells were washed 3 times in 0.1% Triton X-100/PBS, 3 minutes each.

Rabbit anti-E-cadherin antibody (Santa Cruz Biotech, Calif.) was diluted ¹⁄₁₀₀ in 5% BSA/PBS and added to the cells on coverslips for 2 hours. Cells were washed 5 times in 0.1% Triton X-100/PBS, 3 minutes each. Secondary antibody, Alexa Fluor 488 chicken anti-rabbit was diluted $\frac{1}{200}$ in 5% BSA/PBS and added to coverslips for one hour in the dark. Cells were washed five times in 0.1% Triton X-100/PBS, three minutes each. Cells were washed in PBS for one minute and placed in Hoechst (1 mg/ml), diluted $\frac{1}{1000}$, for 5 minutes. Cells were washed in PBS for one minute. SlowFade was added to slides, coverslips were placed face down and sealed with nail polish. Cells were viewed at the Center for Cell Analysis and Modeling, University of Connecticut Health Center, Farmington, Conn., with an Axioplan CCD Microscope equipped with a 40×1.3 NA FL objective lens and Photometrics PXL-EEV37 high speed digital cooled CCD camera via Metamorph image acquisition and analysis software (Universal Imaging Corp., Downington, Pa.).

Immunofluorescence of β-catenin was performed as described for E-cadherin. Nonspecific sites were blocked with donkey serum. Primary antibody, goat anti-β-catenin antibody (Santa Cruz Biotech, Calif.) was diluted $\frac{1}{100}$ in 5% BSA/PBS. Secondary antibody, Alexa Fluor 568 donkey anti-goat antibody was diluted $\frac{1}{200}$ in 5% BSA/PBS.

Immunofluorescence of N-cadherin was performed as described for E-cadherin. Nonspecific sites were blocked with chicken serum. Primary antibody, rabbit anti-N-cadherin (Santa Cruz Biotech, Calif.) was diluted $\frac{1}{100}$ in 5% BSA/PBS. Secondary antibody, Alexa Fluor 488 chicken anti-rabbit antibody was diluted $\frac{1}{200}$ in 5% BSA/PBS.

Immunofluorescence of p27

Cells were grown on 12 mm coverslips until 60 to 70% confluent. 2% methyl sulfone was added to half the coverslips and normal medium to other half. After 24, 48, and 96 hours, coverslips were placed in porcelain holders and incubated in 37° C. PBS for 30 seconds followed by incubation in 37° C. 4% paraformaldehyde for 10 minutes. Cells were washed in PBS for 5 minutes followed by incubation in 0.2% Triton X-100/PBS for 5 minutes at room temperature. Chicken serum (50 ml in 1 ml PBS) was added to cells for 30 minutes. Cells were washed 3 times in 0.2% Triton X-100/PBS, 3 minutes each. Rabbit anti-p27 polyclonal antibody, (Santa Cruz Biotech, Calif.) was diluted $\frac{1}{250}$ in 1% BSA/PBS and added to coverslips for 1.5 hours. Cells were washed 5 times in 0.2% Triton X-100/PBS, 3 minutes each. Secondary antibody, Alexa Fluor 488 chicken anti-rabbit antibody, was diluted $\frac{1}{1000}$ in 1% BSA/PBS and added to coverslips for 30 minutes in the dark. Cells were washed five times in 0.2% Triton X-100/PBS, three minutes each. Cells were washed twice in PBS for two minutes each and placed in DAPI, diluted $\frac{1}{1000}$ in PBS, for 5 minutes. Cells were washed in PBS for one minute. SlowFade was added to slides, coverslips were placed face down and sealed with nail polish. Cells were viewed at the Center for Cell Analysis and Modeling, University of Connecticut Health Center, Farmington, Conn., with an Axioplan CCD Microscope equipped with a 100× objective lens and Photometrics PXL-EEV37 high speed digital cooled CCD camera via Metamorph image acquisition and analysis software (Universal Imaging Corp., Downington, Pa.).

Immunofluorescence of Vimentin

Cells were grown on 12 mm coverslips. After 24 hours, 2% methyl sulfone was added to half the coverslips and normal medium to other half. After 120 hours, coverslips were placed in porcelain holders and cells were fixed in −20° C. methanol for 10 minutes. Cells were washed two times in 0.1% Triton X-100/PBS and incubated in 1% BSA/PBS in a large glass Petri dish lined with water-soaked Kim Wipes and a parafilm bottom for 30 minutes. Cells were incubated in anti-vimentin goat polyclonal (Santa Cruz Biotech, Calif.), diluted $\frac{1}{50}$ in 1% BSA/PBS for 1 hour. Cells were washed 5 times in 0.1% Triton X-100/PBS, 3 minutes each. Secondary antibody, Alexa Fluor 488 rabbit anti-goat was diluted $\frac{1}{100}$ in 1% BSA/PBS and added to coverslips for 30 minutes in the dark. Cells were washed five times in 0.1% Triton X-100/PBS, three minutes each. Cells were washed twice in PBS for two minutes each and placed in DAPI (1 mg/ml), diluted $\frac{1}{1000}$ in PBS, for 5 minutes in the dark. Cells were washed in PBS for one minute. SlowFade was added to a slide, coverslips were placed face down and sealed with nail polish. Cells were viewed at the Center for Cell Analysis and Modeling, University of Connecticut Health Center, Farmington, Conn., with an Axioplan CCD Microscope equipped with a 100× objective lens and Photometrics PXL-EEV37 high speed digital cooled CCD camera via Metamorph image acquisition and analysis software (Universal Imaging Corp., Downington, Pa.).

Immunofluorescence of Microtubules

Cells were plated in 6-100 mm tissue culture plates, each containing 1 polylysine-coated 10-well slide, or plated onto polylysine-coated coverslips. Once cells were approximately 50% confluent, 2% methyl sulfone was added to cells for 10, 30, 60, 90, and 120 minutes. At each time point cells were placed in microtubule stabilizing buffer ( ) for 10 minutes followed by incubation in −20° C. methanol for 5 minutes. Cells were washed twice in 0.1% Triton X-100 in PBS at room temperature, then incubated with mouse monoclonal anti-alpha-tubulin antibody (Santa Cruz Biotech, Calif.; diluted $\frac{1}{200}$ in 1% BSA/PBS) for 1.5 hours. Cells were washed 5 times in 0.1% Triton X-100/PBS, 3 minutes each. Cells were incubated with secondary antibody (Alexa Fluor 568 rabbit anti-mouse antibody; diluted $\frac{1}{100}$ in 1%/PBS) for 30 minutes in the dark. Cells were washed five times in 0.1% Triton X-100/PBS, three minutes each. Cells were washed two times in PBS at 2 minute intervals and incubated with DAPI (1 μg/ml in PBS) for 5 minutes at room temperature and in the dark. Cells were washed in PBS for one minute. SlowFade was added to glass slides, coverslips were placed cell side down and sealed with nail polish. Microtubules were viewed at the Center for Cell Analysis and Modeling, University of Connecticut Health Center, Farmington, Conn., with an Axioplan CCD Microscope equipped with a 40×1.3 NA FL objective lens and Photometrics PXL-EEV37 high speed digital cooled CCD camera via Metamorph image acquisition and analysis software (Universal Imaging Corp., Downington, Pa.).

Soft Agar Assay for Colony Formation

Cells were plated on 8-35 mm plates that contained base agar with and without 2% methyl sulfone. To make base agar, 1% agar (DNA grade; Difco Bacto Agar; Becton Dickenson and Company, Sparks, Md.), was mixed in water at room temperature, melted in a microwave, and cooled to 40° C. before using. For drug plates, 1% agar was combined (1:1) with 4% methyl sulfone in 2×RPMI medium with sodium bicarbonate supplemented with 10% FBS and 5% penicillin/streptomycin. For control plates, 1% agar was combined (1:1) with 2×RMPI medium. Agar +/−2% methyl sulfone was added to appropriate 35 mm tissue culture plates and stored overnight at 4° C. The next day top agar and cells were placed on top of the base agar. Top agar was made with 0.66% agar in water. The agar was melted in a microwave, cooled, and stored at 40° C. 2×RPMI medium and 4% methyl sulfone was also stored at 40° C. Cells were trypsinized and counted for a final concentration of $5×10^3$ cells/plate. Cell counts were adjusted to $2×10^5$ cells/ml and 0.05 ml of the cell suspension was added to 15 ml centrifuge tubes (2 each). Base agar plates were removed from 4° C. and allowed to warm to room temperature for approximately 30 minutes prior to plating. For plating control cells, 2×RPMI medium and 0.66% agar were added to the tube of cell suspension, gently mixed, and placed on top of control base agar plates. For plating cells in 2% methyl sulfone, 4% methyl sulfone (in 2×RMPI medium) and 0.66% agar was added to the tube of cell suspension, mixed gently, and placed on top of the drug base agar plates. Cells were incubated in the 37° C., 5% $CO_2$ incubator for 10-14 days. Plates were stained with 0.005% crystal violet for 1 hour. Colonies were photographed and counted with a dissecting microscope.

Cell Invasion Assay

Invasion assays were performed in Transwell chambers (Corning). The 8 μm pore membranes of the upper chambers were coated with ECM gel from Engelbreth-Holm-Swarm murine sarcoma (Sigma), diluted 1:6 with RPMI medium +/−2% methyl sulfone, and placed in a well with RPMI medium +/−2% methyl sulfone. Cells ($1 \times 10^5$ cells/200 μl) were seeded into appropriate upper chambers in RMPI medium+/−2% methyl sulfone. After 20 hours of incubation at 37° C., cells were removed from top surface of the chamber and filters were fixed with 5% glutaraldeyde. Cells on the lower surface of the filter were stained with a 0.5% solution of toluidine blue. Membranes of inserts were removed with a razor, mounted between a glass slide and a coverslip, and held in place with scotch tape. Cells were photographed and counted at the Center for Cell Analysis and Modeling, University of Connecticut Health Center, Farmington, Conn., with an Axioplan CCD Microscope equipped with a 40×1.3 NA FL objective lens and high speed digital cooled CCD camera via Metamorph image acquisition and analysis software (Universal Imaging Corp., Downington, Pa.). All assays were performed in triplicate.

Cell Wounding

Cells were cultured to approximately 90% confluence in 35 mm tissue culture plates. Methyl sulfone (2%) was added to half the plates and 48 hours later cells were wounded with a sterile plastic 1000 μl pipette tip. Cells were washed two times with medium to remove cell debris and incubated at 37° C. over night in RMPI medium +/−2% methyl sulfone. After 72 hours, wound edges were photographed and recorded with a Nikon TE300 inverted microscope (Nikon) equipped with a 10×0.25 NA Plan Achromat objective lens. Time-series (5 min long) of phase contrast images were acquired at a video rate (1 frame/3s) with a Watec-902B CCD video camera (Watec Corp., Japan) via stream acquisition option of Metamorph image acquisition and analysis software (Universal Imaging Corp., Downington, Pa.). During the recordings, cells were kept at 37° C. and 10 mM Hepes. Time series and photographs of cells +/−2% methyl sulfone were obtained every 24 hours for up to 120 hrs.

Mitochondrial Staining: Live and Fixed Cells

Cells were grown on 12 mm round coverslips treated with polylysine to 60-90% confluence. After 24 hours, 2% methyl sulfone was added to half the coverslips. At 48 and 72 hours, 500 nM MitoTracker Red CM-$H_2$XRos (Molecular Probes, Eugene, Oreg.), diluted in medium +/−2% methyl sulfone, was added to cells and cells were incubated for 45 minutes at 37° C. Fresh medium +/−2% methyl sulfone was added to cells and cells were photographed using a Nikon TE300 inverted microscope (Nikon) equipped with a 20×NA Plan Achromat objective lens. Phase contrast images were acquired with a Watec-902B CCD video camera (Watec Corp., Japan). Fluorescence images of Rhodamine-labeled mitochondria were obtained with Andor iXon EM-CCD (Andor Technology, Windsor, Conn.). Both cameras were driven by Metamorph image acquisition and analysis software (Universal Imaging, Downington, Pa.).

For fixed cells, cells were washed in medium after incubation in MitoTracker Red, then placed in 3.7% formaldehyde in 37° C. medium +/−2% methyl sulfone for 15 minutes at 37° C. Cells were washed in PBS several times, 3 minutes each, then added to ice cold acetone using a porcelain holder. After one wash in PBS for one minute, SlowFade was added to a slide, coverslips were placed face down and sealed with nail polish. Images were obtained at the Center for Cell Analysis and Modeling, University of Connecticut Health Center, Farmington, Conn., USA, with an Axioplan CCD Microscope equipped with a 63× objective lens and Photometrics PXL-EEV37 high speed digital cooled CCD camera via Metamorph image acquisition and analysis software (Universal Imaging Corp., Downington, Pa.).

Senescence Assay

Senescence was assessed with the Senescence Cells Histochemical Staining Kit (Sigma).

Results

Dose Response of Melanoma Cells to Methyl Sulfone

M3 Cloudman melanoma cells were plated into culture dishes containing RPMI medium. After 24 hour media was changed to control medium (no drug) or to media containing different concentrations of methyl sulfone (1-10% methyl sulfone in RPMI medium). Cells were examined by live cell video microscopy immediately after adding drug and every 24 hours up to 144 hours.

Figure 2:
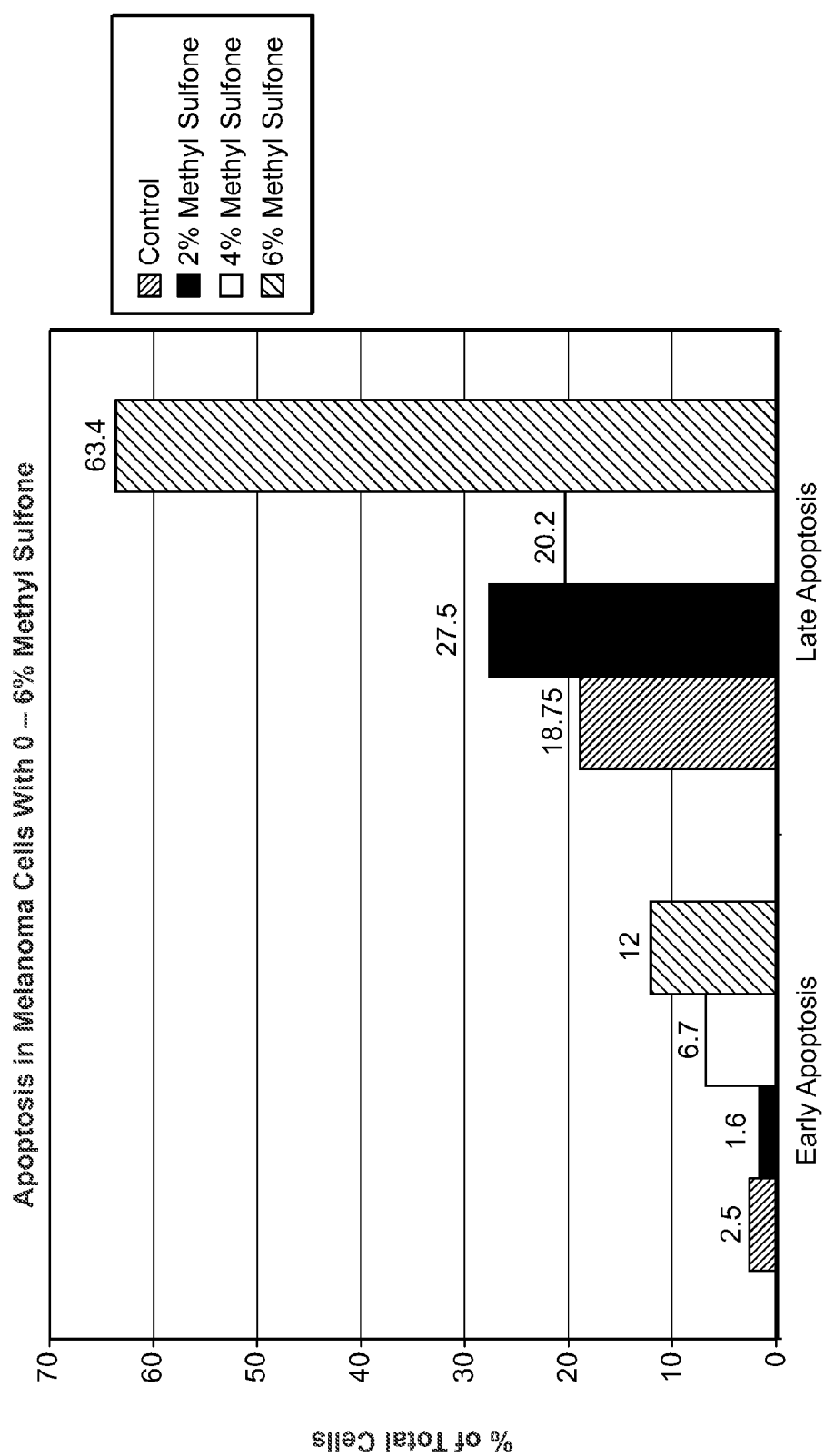
FIG. 2 depicts a graph demonstrating apoptosis in melanoma cells with 0-6.0 percent methyl sulfone.

Immediately after adding the drug at all concentrations, cells became round with some cells detaching from culture plates (FIG. 1). When melanoma cells were incubated with 2-6% methyl sulfone for 24 hours, the cells treated with the higher concentration (6%) were induced into apoptosis (FIG. 2). However, at 2% methyl sulfone, cells re-attached to the culture dish over the next few hours and took on a morphology distinct from control cells: cells in 2% methyl sulfone displayed a flattened morphology compared with the amorphous worm-like shape of untreated cells.

The possibility that the data generated from treating cells with methyl sulfone was a nonspecific effect due to changes in extracellular osmolarity was considered. To test this possibility an equimolar concentration of urea was substituted for 2% methyl sulfone; urea has a chemical structure and dipolar moment that is similar to methyl sulfone. Urea did not mimic the effects of methyl sulfone. Instead urea induced necrotic death. We next replaced 2% methyl sulfone with an equimolar concentration of dimethyl sulfoxide (DMSO). Microscopic analysis demonstrated that DMSO had no effect on the melanoma cells and did not induce any of the effects observed with methyl sulfone.

Methyl Sulfone Induced Contact Inhibition in Melanoma Cells

Figure 3:
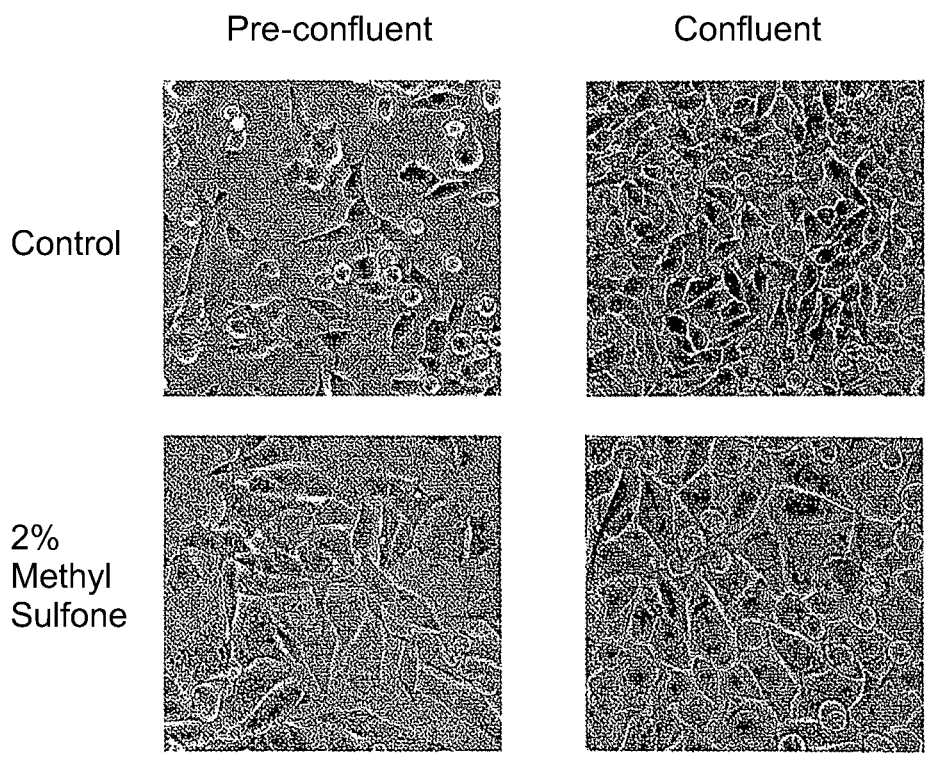
FIG. 3 depicts melanoma cells with and without 2% methyl sulfone.

By 24 hours after adding 2% methyl sulfone, cells grew until they came in touch with neighboring cells. At this point cells appeared to be contact inhibited (FIG. 3). Live cell video demonstrated that while control cells retained their amorphous rounded shapes and continued to migrate over neighboring cells, melanoma cells in 2% methyl sulfone stopped migration and growth, and formed a confluent monolayer of quiescent, G1 arrested cells, a hallmark for contact inhibition.

Methyl Sulfone Inhibited DNA Synthesis in Melanoma Cells

Figure 4:
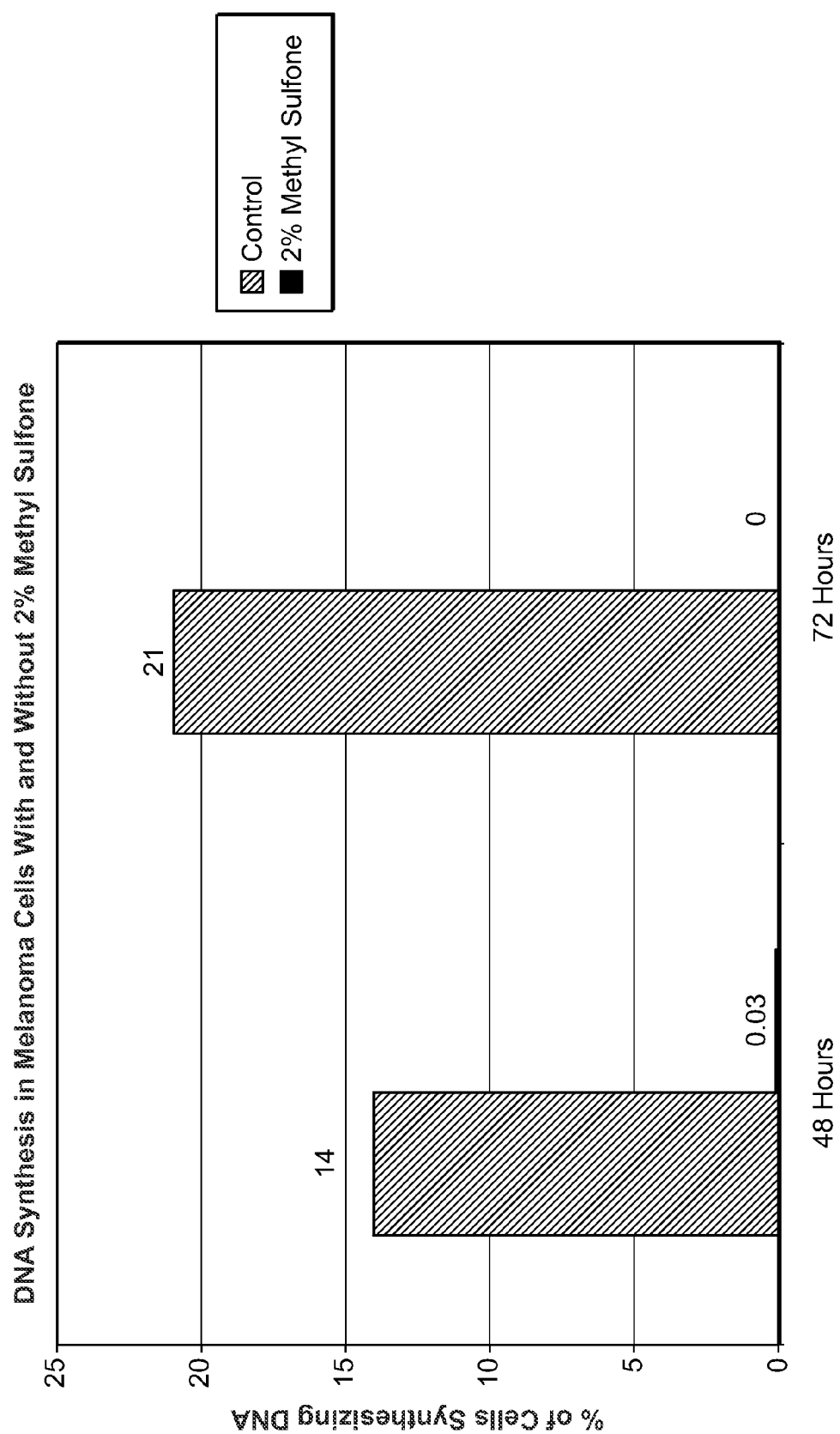
FIG. 4 is a graph depicting DNA synthesis in melanoma cells with and without 2% methyl sulfone at 48 and 72 hours.

When cells become quiescent, then DNA synthesis decreases significantly compared to cells that remain in the cell cycle. To compare DNA synthesis in control cells and cells treated with 2% methyl sulfone, the percentages of incorporation of BrdU into DNA was determined FIG. 4 demonstrates data from cells at 48 and 72 hours in the presence or absence of 2% methyl sulfone. At 48 hours, 14% of control cells were synthesizing DNA while only 0.03% of cells in 2% methyl sulfone were synthesizing DNA. At 72 hours, 21% of control cells and 0% of drug-treated cells were synthesizing DNA.

Melanoma Cells Became Anchorage-Dependent in the Presence of 2% Methyl Sulfone

Malignant cells do not require attachment or anchorage to a hard substrate for growth. This anchorage-independence is a classic characteristic of metastatic cells. Colony formation from cell proliferation occurs when cancer cells are grown on soft agar, whereas normal cells will not proliferate and therefore will not form colonies on soft agar. Methyl sulfone was tested to determine if it affected anchorage-independent growth of the melanoma cells using the soft agar assay. As shown in FIG. 5, treatment of melanoma cells with 2% methyl sulfone resulted in no colony formation, whereas hundreds of colonies formed with control cells.

Figure 6:
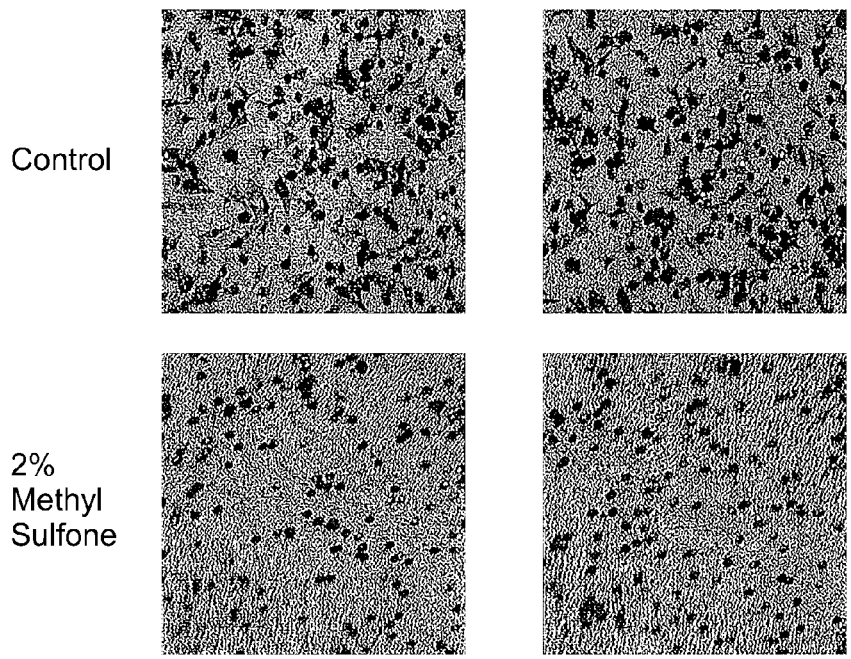
FIG. 6 depicts the migration of melanoma cells through a matrix membrane after being treated with 2% methyl sulfone for 48 hours. Dark spots are membrane pores. Melanoma cells are lightly colored and triangular. In the presence of 2% methyl sulfone, melanoma cells are unable to pass through the membrane.

Methyl Sulfone Inhibited Migration of Melanoma Cells Through an Extracellular Matrix A second classic characteristic of metastatic cells is their ability to migrate through an extracellular matrix. We determined whether methyl sulfone altered this ability in melanoma cells. In the absence of methyl sulfone, a large percentage of cells migrated through the matrix. In contrast none of the cells treated with 2% methyl sulfone migrated through the matrix (FIG. 6).

Wound Healing Proceeded Normally in the Presence of Methyl Sulfone

Figure 7:
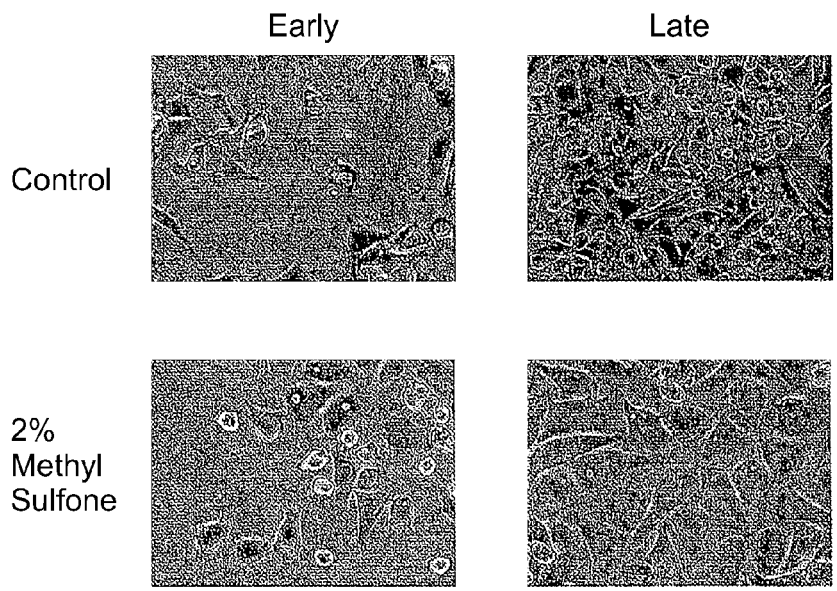
FIG. 7 depicts wound healing in melanoma cells in the presence and absence of 2% methyl sulfone.

Wound healing is a complicated process in which cells juxtaposed to a wound site must detach from neighboring cells and from a substrate (or basement membrane), migrate into the wound and then become contact inhibited once the wound is covered. We tested whether melanoma cells treated with 2% methyl sulfone would function properly in the process of wound healing. As described in herein, control melanoma cells and cells treated with 2% methyl sulfone were grown to confluence. Scraping a layer of confluent cells with a plastic pipette tip formed wounds. Live cell video microscopy was used to monitor migration of cells into the wound. In control samples, cells migrated into the wound area, but did not stop moving once the wound site was covered, forming a tumor-like mass at the wound site. In contrast, melanoma cells treated with 2% methyl sulfone detached from neighboring cells and from the tissue plate surface and migrated into the wound area, albeit at a slower rate than control cells. However, in contrast to control cells, when the wound was covered, cells treated with 2% methyl sulfone stopped migrating and once again became contact inhibited (FIG. 7).

Methyl Sulfone Induced Senescence in Melanoma Cells

Figure 8:
FIG. 8 depicts 2% methyl sulfone induced senescence in melanoma cells. Virtually non control cells were senescent.

During the first 2-3 weeks of incubating melanoma cells in 2% methyl sulfone, replacement of the 2% methyl sulfone medium with medium without drug reversed the phenotypes described above. Re-adding 2% methyl sulfone to the cells re-induced the non-malignant phenotypes. This cycle of reversal occurred until the cells were incubated with 2% methyl sulfone for more than three weeks. At this point greater than 95% of the melanoma cells became senescent as judged by activation of β-galactosidase activity that turned senescent cells blue (FIG. 8). Senescence indicates that cells can never re-enter the cell cycle. To determine whether the increase in β-galactosidase activity truly indicated senescence, we replaced medium containing 2% methyl sulfone with control medium on cells that the β-galactosidase assay indicated were senescent and we found that the cells remained senescent. As a further test, we detached senescent cells from the culture dish by trypsinization and replated the cells in medium without methyl sulfone. The cells reattached to the culture dish, became contact inhibited and remained senescent as judged by β-galactosidase activity.

Methyl Sulfone Induced Arborization of Senescent Melanoma Cells

Mature melanocytes assume a morphology that is similar to neuronal cells by having a small area of cytoplasm surrounding the nucleus and long extensions called arbors. The primary function of melanocytes is to produce melanin and package the melanin in vesicles called melanosomes. Melanosomes are then transported to the tips of melanocytes arbors. These tips are phagocytized by keratinocytes, cells that sit near the skin's surface, and the newly acquired melanosomes form an umbrella-like shield around the nuclei of keratinocytes to protect these cells' DNA from UV-inducing mutations.

Figure 9:
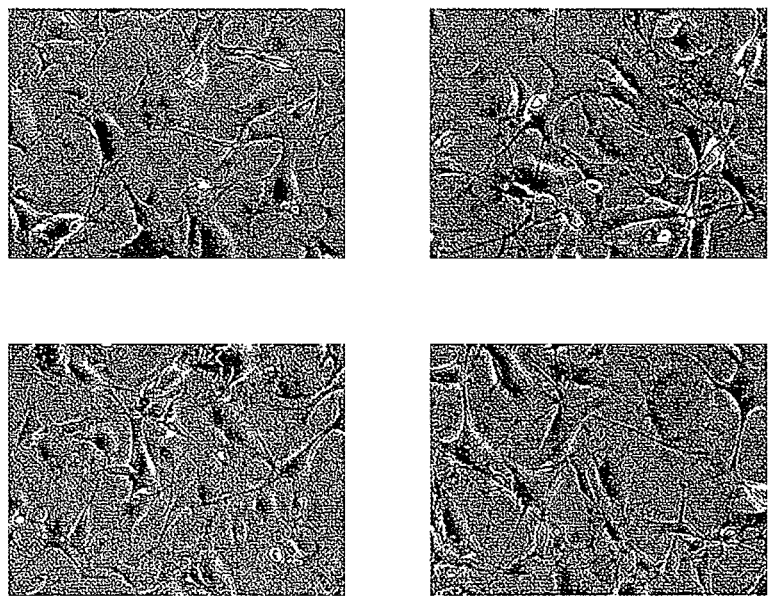
FIG. 9 depicts four different fields of the arborized cells. The dark arbors indicate the presence of melanosomes.

Melanoma cells that have become senescent in the presence of 2% methyl sulfone took on the morphology of mature melanocytes complete with extensive arbors that were filled with melanosomes (FIG. 9). These cells survived in culture for at least two months.

p27 was Localized in Nuclei of Melanoma Cells Treated with Methyl Sulfone p27 is a protein associated with cell cycle arrest and senescence. Its active form is found inside the nucleus. Using immunofluorescent microscopy, we showed that p27 is localized in the nuclei of cells treated with methyl sulfone.

Methyl Sulfone Did not Alter Proteins Involved in the Epithelial to Mesenchymal (ETM) Transition.

Figure 10:
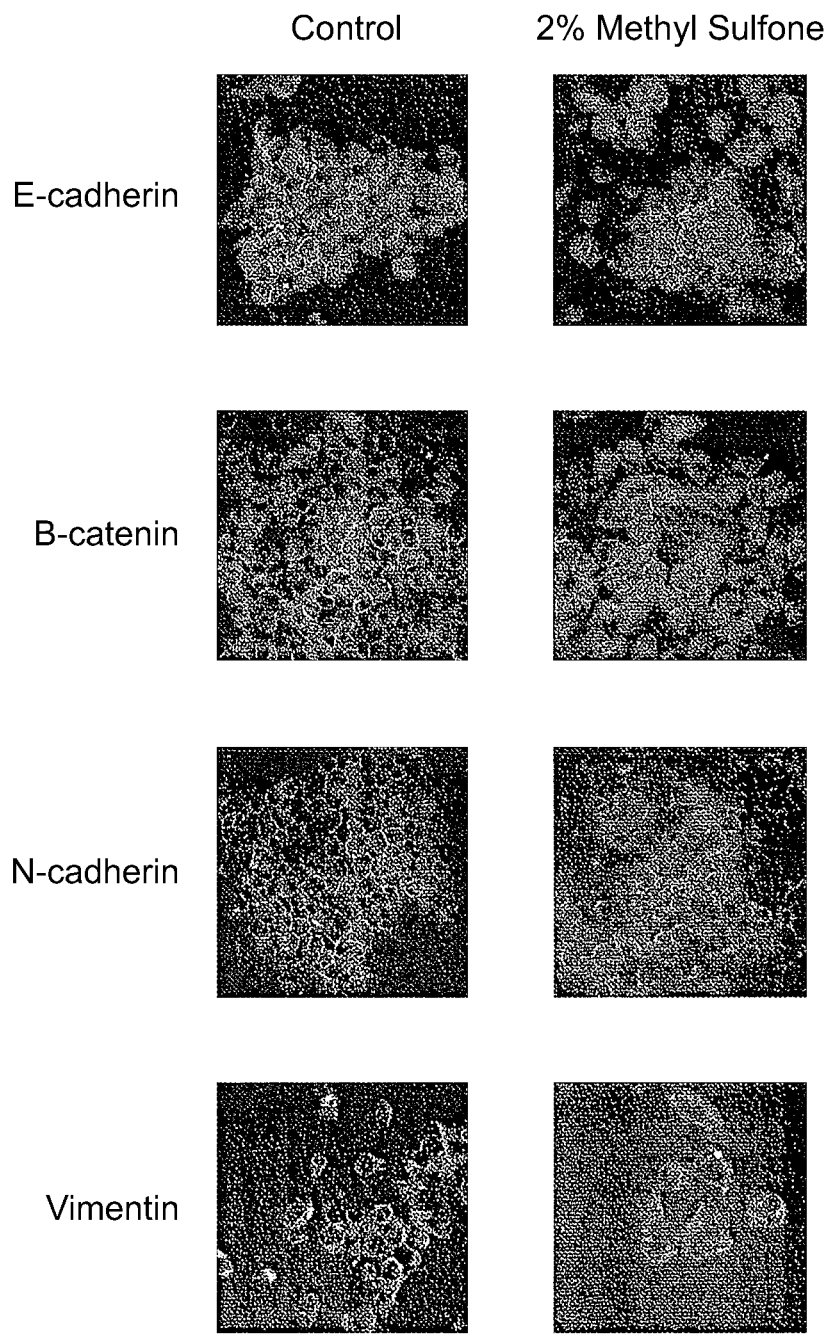
FIG. 10 depicts immunofluorescensce microscopy of proteins involved in the ETM transition. Shown are melanoma cells with and without 2% methyl sulfone after seven days.

The ETM Transition may be involved in development of metastasis of some tumors. Proteins associated with epithelial cells include E-cadherin and β-catenin, while proteins associated with mesenchymal cells include N-cadherin and vimentin. We used immunofluorescence microscopy to compare the distribution of E-cadherin, β-catenin, N-cadherin and vimentin in melanoma cells with and without treatment with methyl sulfone. As shown in FIG. 10, there were no significant differences in the distribution of these proteins in melanoma cells in the presence or absence of 2% methyl sulfone after treatment with drug for 1 week. Similar results were found after incubation of melanoma cells with 2% methyl sulfone for 5 weeks.

Effect of Methyl Sulfone on Actin Filaments and Microtubules

Figure 11:
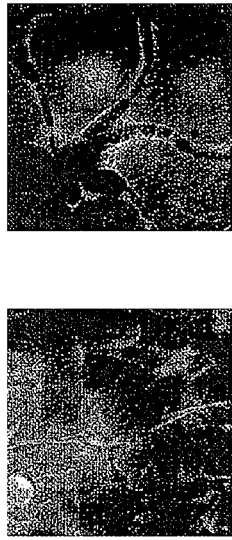
FIG. 11 depicts immunofluorescence microscopy of actin filaments in melanoma cells with and without 2% methyl sulfone after 72 hours.

Immunofluorescence of actin filaments did show differences between cells incubated with and without the drug. In control cells, actin filaments were found primarily in leading edge extensions. In cells treated with 2% methyl sulfone, actin filaments were clearly visible at the cell surface in small protrusions that contacted neighboring cells (FIG. 11).

Figure 12:
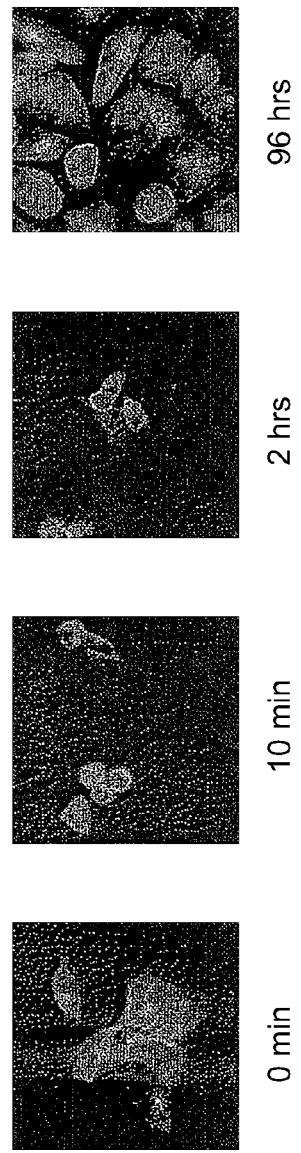
FIG. 12 depicts immunofluorescence microscopy of microtubles in melanoma cells in the presence of 2% methyl sulfone over time.

Immunofluorescence of microtubules demonstrated that within 10 minutes of adding 2% methyl sulfone to melanoma cells, the microtubules rapidly disassembled. Over the next two hours, microtubules began to reassemble, but in a pattern distinct from untreated cells. In control cells, microtubules were found primarily in "growth cone-like" extensions, with an appearance of disorder within the cytoplasm. In cells treated with 2% methyl sulfone, microtubules reappeared in an orderly pattern, emanating from microtubule organizing centers and radiating outward toward the cell periphery (FIG. 12).

Figure 13:
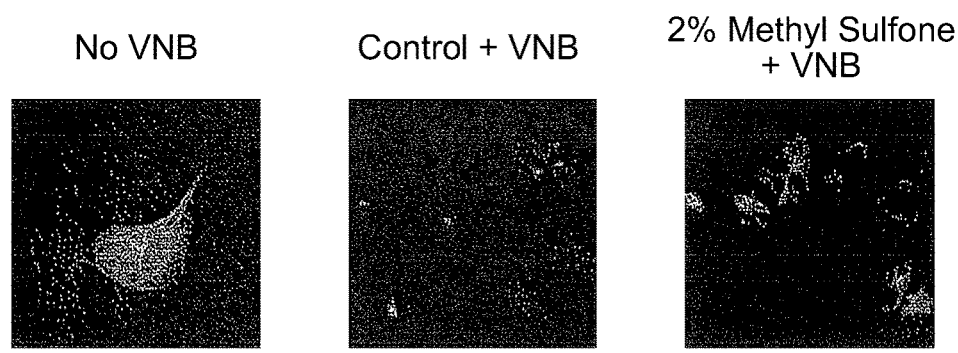
FIG. 13 depicts immunofluorescence microscopy of microtubules in melanoma cells with an without 2% methyl sulfone in the presence of $10^{-7}$M vinblastine (VNB). Cells were processed for immunofluorescence two hours after adding VNB.

One assay to test stability of microtubules is to give cells increasing concentrations of a microtubule-disassembly drug and use immunofluorescence microscopy to assess microtubule lengths (Caron et al). A higher concentration of drug will be required to disassemble the more stabilized microtubules. We used different concentrations of the anti-microtubule drug, vinblastine, to assess microtubule stability in control cells and cells incubated with 2% methyl sulfone. At a concentration of $10^{-7}$ M vinblastine, microtubules in control cells were largely gone, whereas microtubules in cells treated with 2% methyl sulfone were clearly visible (FIG. 13). These data suggest that methyl sulfone stabilizes microtubules.

Effects of Methyl Sulfone on Melanoma Cells were Also Found in Aggressive and Metastatic Estrogen Receptor-Negative Breast Cancer Cells We found that concentrations of methyl sulfone above 2% induced apoptosis in breast cancer cells. When breast cancer cells were treated with 2% methyl sulfone, cells became contact inhibited, DNA synthesis was markedly reduced, mitochondrial activity decreased, cell growth became anchorage-dependent, migration of cells through an extracellular matrix was inhibited, wound healing proceeded normally, and cells became senescent.

Methyl Sulfone Induced Apoptosis in Leukemic T-Cell Lymphocytes, but not in Normal T-Cell Lymphocytes Leukemic Lymphocytes CEM cells, leukemic T-cell lymphocytes obtained from a six-year old girl with acute lymphocytic leukemia, were maintained in Petri dishes in MEM (minimal essential medium) with 7% fetal calf serum in a 5% $CO_2$ incubator at 37° C. For experiments, methyl sulfone was added to the medium at concentrations from 0-6.0%. In control cells, no methyl sulfone was added. Cells ($2 \times 10^6$ per ml) were incubated for 20 hrs in the presence or absence of methyl sulfone, and then assayed for apoptosis using FITC-annexinV/propidium iodide microscopy. Methyl sulfone was also compared to the anti-microtubule drug, vinblastine. Vinblastine (VNB) and its derivative, vincristine, are standard treatments for acute lymphocytic leukemia, as well as other cancers. We used the concentration of VNB that is found in the blood of subjects being treated with this drug ($10^{-7}$ M) (6,7).

After 20 hours, 74% of the leukemic lymphocytes in 4% methyl sulfone were apoptotic. In 6% methyl sulfone, 88% of the cells were apoptotic.

Figure 14:
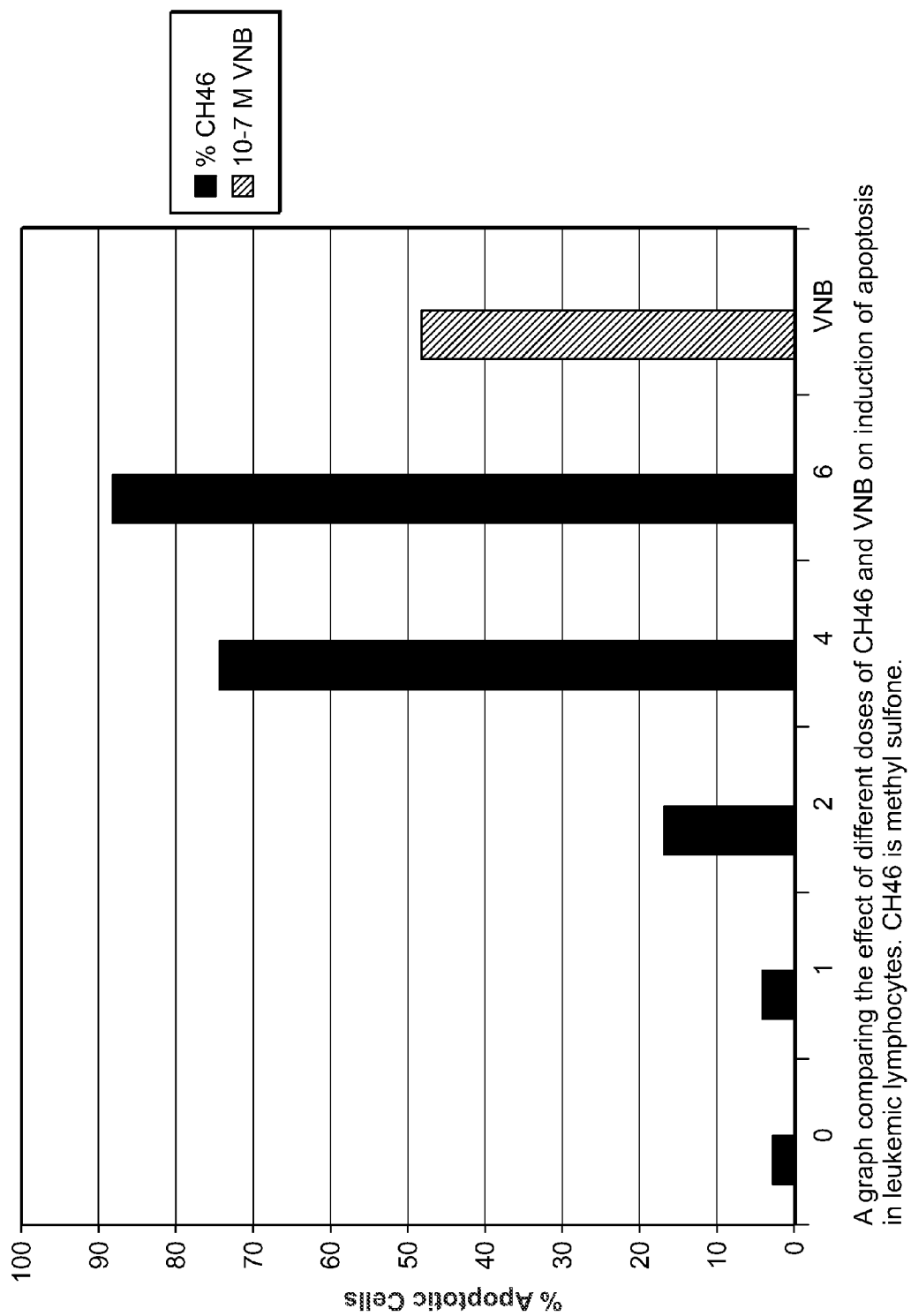
FIG. 14 is a graph comparing the effect of different doses of methyl sulfone and VNB on induction of apoptosis in leukemic lymphocytes. CH46 is a clinical name for methyl sulfone.

After 20 hours in $10^{-7}$ M VNB, 48% of the leukemic cells were apoptotic (FIG. 14).

Normal Lymphocytes

Blood was drawn from healthy volunteers and white blood cells (e.g., lymphocytes, neutrophils) were enriched using Ficoll-Plaque. Cells were incubated in Petri dishes containing MEM with 7% fetal calf serum in a $CO_2$ (5%) incubator at 37° C.; Methyl sulfone was present at concentrations of 0, 3, 6, or 10%. After 20 hours, cells were incubated with antibodies specific to T-lymphocytes (CD3 and CD4 T-cells), B-lymphocytes (B-cells) and neutrophils, and the percent of apoptotic cells was determined by Flow Cytometry. This is a technique that identifies specific cell types (e.g., CD3 T-cells, CD4 T-cells, B-cells, neutrophils) within a mixed population of blood cells, and then determines whether the cells are alive or apoptotic.

CEM leukemic lymphocytes were also incubated in the presence or absence of 10% methyl sulfone. The goal here was to determine whether the FITC-annexinV/propidium iodide microscopy assay described above produced similar results as the Flow Cytometry assay used in these experiments.

Figure 15:
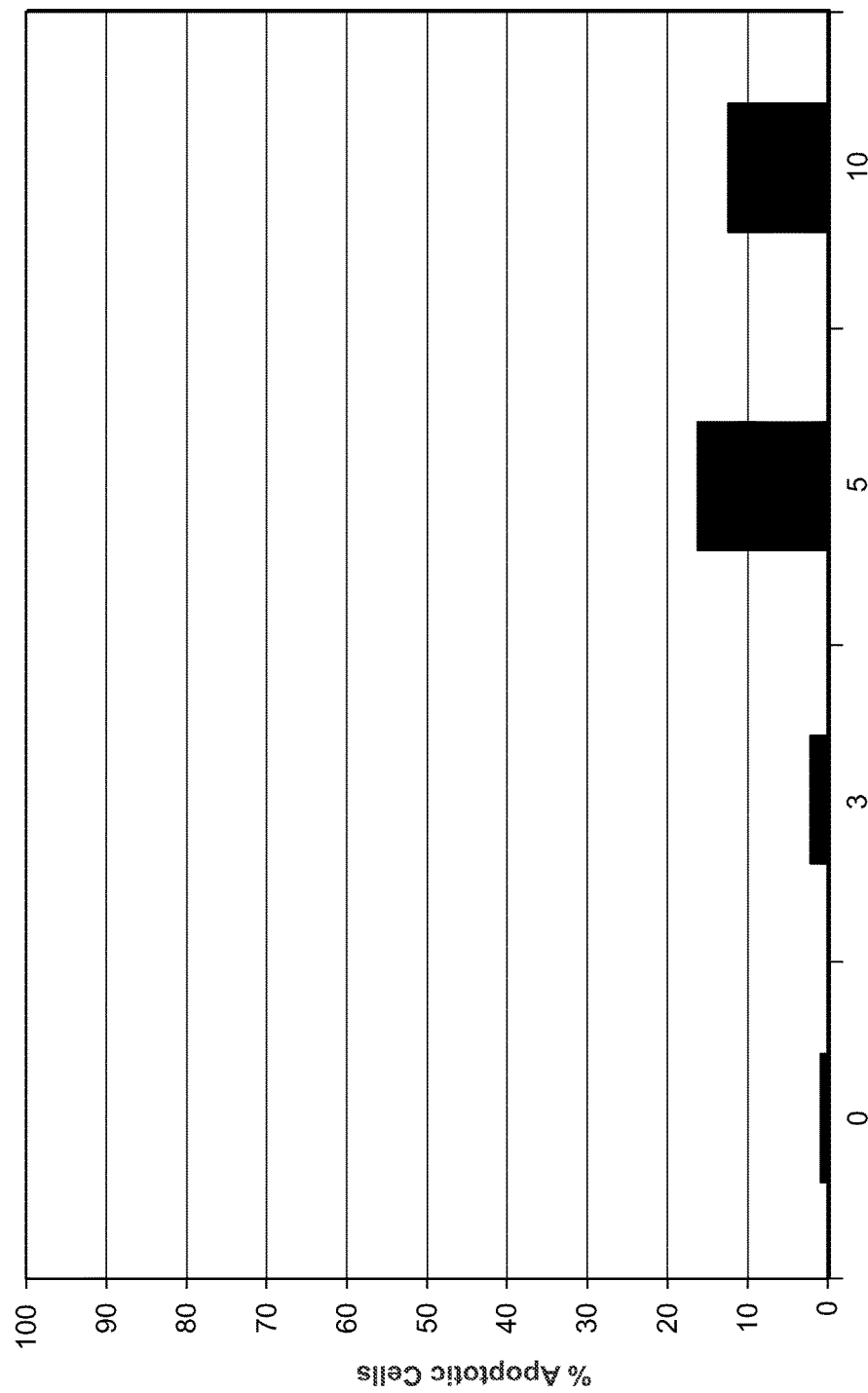
FIG. 15 depicts normal lymphocytes from a healthy volunteer were treated with different doses of methyl sulfone and percent apoptotic cells were determined by flow cytometry CH46 is a clinical name for methyl sulfone.

After 20 hours, cells were incubated with fluorescent antibodies to identify T-cells, B-cells and neutrophils, and then processed by Flow Cytometry (FIG. 15).

Even at 10% methyl sulfone, normal lymphocytes (T-cells) remained viable. B-cells and neutrophils were also unharmed by 10% methyl sulfone. In contrast, 92% of the CEM leukemic lymphocytes were killed by 10% methyl sulfone. These data indicate, first, that methyl sulfone was harmful to leukemic lymphocytes, but not to normal lymphocytes. Second, the two apoptotic assays (microscopy and Flow Cytometry) produced similar results. Third, methyl sulfone was more effective than vinblastine, the chemotherapeutic drug used today against leukemia and other cancers.

Methyl Sulfone and Lack of Toxicity

In order to test the toxicity of MMS and structurally related compounds were analyzed for the ability to induce apoptosis in melanoma cells.

Figure 16:
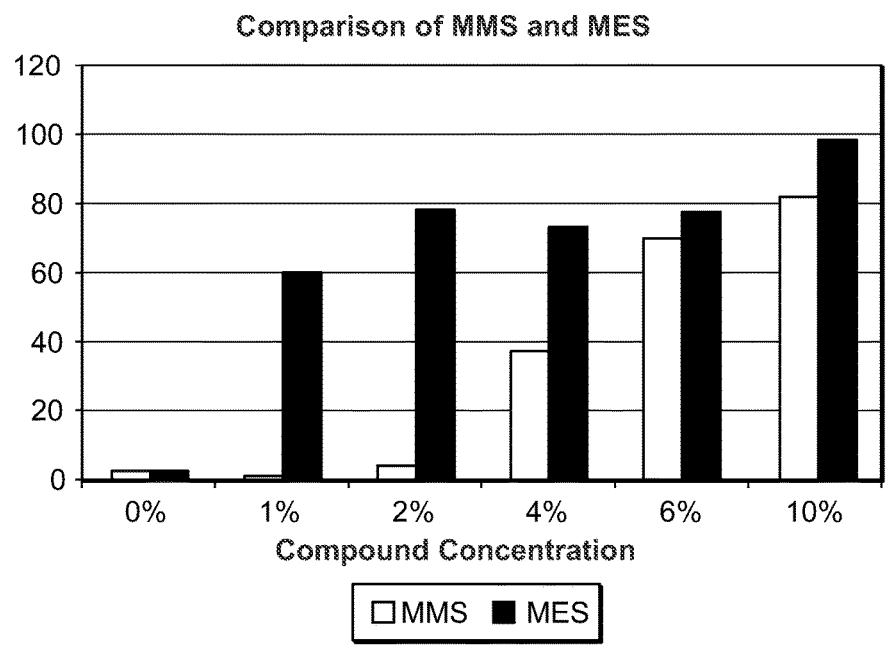
FIG. 16 depicts a comparison of effect on apoptosis of melanoma cells by methyl methyl sulfone (MMS) and methyl ethyl sulfone (MES).
Figure 17:
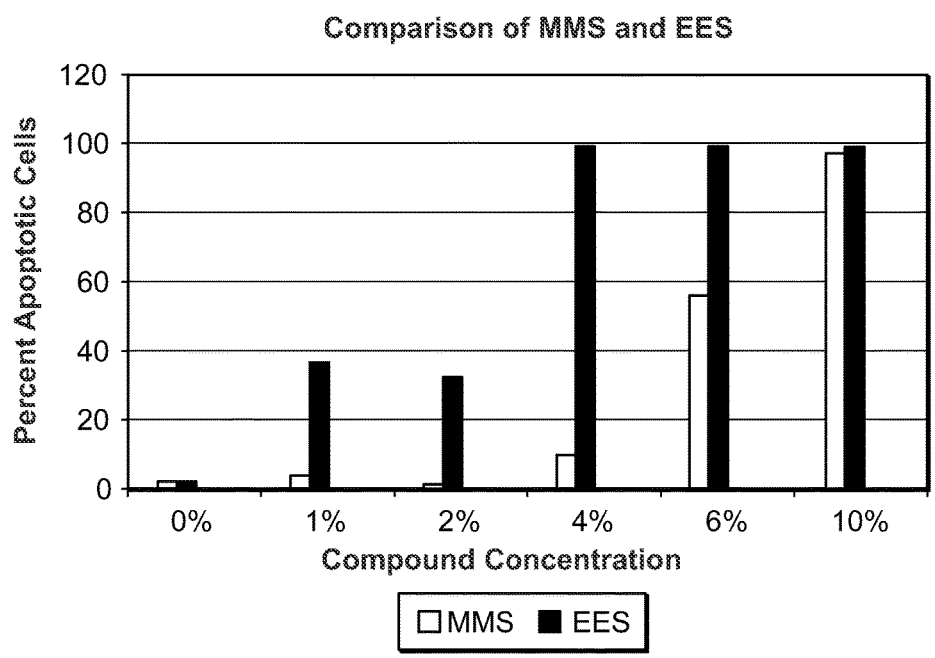
FIG. 17 depicts a comparison of effect on apoptosis of melanoma cells by methyl methyl sulfone (MMS) and ethyl ethyl sulfone (EES).

Briefly, melanoma cells (Cloudman M3 cell line) were plated at $10^5$ cells/ml in RPMI medium. After 24 hours, medium was replaced with RPMI containing different concentrations (grams/volume) of MMS, MES and EES. After 24 hours, apoptosis was assayed using the Becton-Dickinson Annexin V-FITC/Propidium Iodide Kit and a Nikon fluorescent microscope as described by the manufacturer. Results are set forth in FIGS. 16 and 17.

These experiments demonstrate that MMS induces significantly less apoptosis of M3 cells than either MES or EES. This is especially true at the lower concentrations, for example, less than 5% MES, EES, and MMS.

Like most other chemotherapeutic drugs, it appears that EES/MES have a narrow differential (very small window) between killing cancer cells, but also harming normal cells. In contrast, MMS has a wide window of concentrations that kill cancer cells without harming normal cells.

Example 2: Immunofluorescence of SKP2 and p27 in Cancer Cells

SKP2 is a ubiquitin ligase that is active in cell nuclei and is expressed in many types of malignant cells. SKP2 promotes cell cycling and cell proliferation and promotes the degradation of the tumor suppressor protein p27. p27 is a tumor suppressor that is active when located in cell nuclei and in a non-phosphorylated form. p27 promotes cell cycle arrest and senescence.

In normal differentiated cells, p27 (non-phosphorylated active form) is located in the nucleus. In 66 and M3 cells used in this experiment, p27 is in the nuclei and SKP2 is in the cytoplasm in its inactive form. Normal cells have high levels of p27 in nucleus and low levels of SKP2 in the cytoplasm. This was confirmed in the experiments described below. The nuclei were stained with DAPI (blue) and corresponding p27 (red) or SKP2 (red), and then merged the p27/DAPI and SKP2/DAPI photos. In malignant cells, the opposite is true: p27 (phosphorylated and inactive) is in low levels in the cytoplasm; SKP2 (active) is in high levels the nuclei.

Cells were plated at $1 \times 10^5$ cells/ml on 12 mm round coverslips in 35 mm tissue culture plates (final volume of media was 1.5 ml/35 mm plate). At 24 hours after plating, media was replaced with fresh media containing 2% methyl sulfone and cells were incubated in media/2% methyl sulfone for four weeks. Media/2% methyl sulfone was changed every Monday, Wednesday, and Friday Immunofluorescence was performed at four weeks after plating to look for the presence of the following proteins: SKP2 and p27 (Santa Cruz Biotechnology). To begin immunofluorescent staining, cells on coverslips were transferred from tissue culture plates to porcelain holders; the porcelain holders were gently placed in a beaker with PBS (37° C.) for 30 seconds to wash the cells. Cells were fixed in a solution of 4% paraformaldehyde (37° C.) for ten minutes, and then washed in PBS for 5 minutes. Goat serum (Santa Cruz Biotechnology) was used in the blocking step. A large glass Petri dish was lined with parafilm. Coverslips were then placed cell side down on a drop (35 µl per coverslip) of goat serum and incubated at room temperature for thirty minutes. Cells were transferred to the porcelain holders and washed in 0.1% Triton X-100/PBS three times at three minutes per wash. Primary antibodies were diluted 1:100 in 5% BSA/PBS and centrifuged for 1 minute to remove any particulates. Coverslips were placed cell side down on 35 µl of primary antibody/coverslip in the parafilm-lined glass Petri dish and incubated for two hours at room temperature. All primary antibodies were rabbit polyclonal. Cells were transferred to the porcelain holders and washed three times in 0.1% Triton X-100/PBS for three minutes each. Secondary antibody, Alexa Fluor 546 goat anti-rabbit (Molecular Probes), was diluted 1:200 in 5% BSA/PBS. Coverslips were placed cell side down on 35 µl of secondary antibody/coverslip in the parafilm-lined glass Petri dish, and incubated for one hour in the dark at room temperature. Cells were transferred to the porcelain holders and washed five times in 0.1% Triton X-100/PBS for three minutes each, followed by PBS for one minute. To stain nuclei, DAPI was diluted 1:1000 in PBS. Coverslips were placed cell side down on 35 µl of DAPI/coverslip in the parafilm-lined glass Petri dish and incubated at room temperature for five minutes in the dark. Coverslips were washed in PBS for one minute and then placed cell side down on 2.5 µl/coverslip of Slow Fade (Molecular Probes) on glass slides. Clear nail polish was applied around the coverslip and left to air dry in the dark for thirty minutes. Cells were stored overnight at 4° C. Slides were viewed on a widefield microscope equipped with a Photometrics PXL-EEV37 high-speed digital camera. Images were acquired with a 40× objective using Molecular Devices MetaMorph software.

The results of the immunoflourescence experiments described herein demonstrate that in the presence of methyl sulfone, there is high expression of p27 in the nucleus and low levels of SKP2 in the cytoplasm demonstrating that methyl sulfone induces a normal phenotype in malignant, metastatic cells.

Incorporation by Reference

The contents of all references, patents, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a metastatic cancer in a subject having the metastatic cancer comprising administering to the subject a therapeutically effective amount of methyl sulfone, thereby treating the cancer, wherein the therapeutically effective amount comprises a solution of methyl sulfone in the range of 0.2 to 0.6 mg methyl sulfone/ml solvent, or 1.0 to 5.0 mg methyl sulfone/ml solvent, and wherein administration of the methyl sulfone to the subject induces cells of the cancer to revert to a normal cellular phenotype from a cancer cell phenotype.

2. The method of claim 1, wherein the cancer is a solid tumor cancer.

3. The method of claim 2, wherein the solid tumor cancer is selected from the group consisting of ovarian, brain, colon, lung, melanoma, bladder, breast or prostate cancer.

4. The method of claim 1, wherein the cancer is a hematological cancer.

5. The method of claim 4, wherein the hematological cancer is leukemia or lymphoma.

6. The method of claim 1, wherein the subject has previously received chemotherapeutic or radiation therapy which was unsuccessful.

7. The method of claim 1, wherein the methyl sulfone is administered systemically.

8. The method of claim 1, wherein the methyl sulfone is administered locally.

9. The method of claim 1, wherein the methyl sulfone is targeted to the location of the cancer.

10. The method of claim 9, wherein the methyl sulfone is formulated in a micro or nanoparticle.

11. The method of claim 1, wherein an area having a solid tumor is sprayed with or bathed in methyl sulfone.

12. The method of claim 11, wherein the solid tumor is removed prior to treatment with methyl sulfone.

13. The method of claim 1, wherein the subject is a mammal.

14. The method of claim 13, wherein the mammal is a human.

15. A method of treating metastatic cancer in a subject having the metastatic cancer, comprising separately administering to the subject:
   a) a solution of methyl sulfone in the range of 0.2 to 0.6 mg methyl sulfone/ml solvent, or 1.0 to 5.0 mg methyl sulfone/ml solvent; and
   b) a chemotherapeutic agent,
   wherein administration of the methyl sulfone to the subject induces cells of the cancer to revert to a normal cellular phenotype from a cancer cell phenotype.

16. The method as claimed in claim 15, wherein the administration of methyl sulfone and the chemotherapeutic agent is simultaneous.

17. The method as claimed in claim 15, wherein the administration of the methyl sulfone and the chemotherapeutic agent is sequential.

18. The method as claimed in claim 15, wherein the chemotherapeutic agent is chosen from the group of: doxil, topotecan, DNA-altering drugs, carboplatin, antimetabolites, gemcitabine, drugs that prevent cell division, vincristine, anti-angiogenic agents, and pazopanib.

19. A method of treating a subject having a metastatic solid tumor surgically removed comprising spraying or bathing the area containing the tumor with a solution comprising methyl sulfone after removal of the tumor and prior to the completion of the surgery, wherein the solution comprises methyl sulfone in the range of 0.2 to 0.6 mg methyl sulfone/ml solvent, or 1.0 to 5.0 mg methyl sulfone/ml solvent, and wherein administration of the methyl sulfone to the subject induces cells of the cancer to revert to a normal cellular phenotype from a cancer cell phenotype.

20. A method of treating metastatic ovarian cancer in a subject having metastatic ovarian cancer, comprising: contacting the ovaries with a solution of methyl sulfone in the range of 0.2 to 0.6 mg methyl sulfone/ml solvent, or 1.0 to 5.0 mg methyl sulfone/ml solvent; thereby treating the metastatic ovarian cancer, wherein administration of the methyl sulfone to the subject induces cells of the cancer to revert to a normal cellular phenotype from a cancer cell phenotype.

21. The method of claim 20, wherein the ovaries are sprayed with the solution of methyl sulfone.

22. A patch for the treatment of skin cancer comprising methyl sulfone of claim 1.

23. The patch of claim 22, further comprising a pharmaceutically-acceptable diluent or carrier.

24. A kit for the treatment of a cell proliferative disorder comprising methyl sulfone of claim 1 and instructions for use.

25. The kit of claim 24, further comprising an applicator.

26. The kit of claim 25, wherein the applicator is a sponge, spray bottle, or aerosolizer.

* * * * *